(12) United States Patent
Kozuka et al.

(10) Patent No.: US 10,055,543 B2
(45) Date of Patent: Aug. 21, 2018

(54) CONTROL METHOD AND STORAGE MEDIUM FOR SEARCHING MEDICAL IMAGES SIMILAR TO A TARGET IMAGE

(71) Applicant: Panasonic Intellectual Property Management Co., Ltd., Osaka (JP)

(72) Inventors: Kazuki Kozuka, Osaka (JP); Kazutoyo Takata, Fukui (JP); Kenji Kondo, Fukui (JP); Toyohiko Sakai, Fukui (JP); Hirohiko Kimura, Fukui (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/266,358

(22) Filed: Sep. 15, 2016

(65) Prior Publication Data

US 2017/0091930 A1 Mar. 30, 2017

(30) Foreign Application Priority Data

Sep. 30, 2015 (JP) .................................. 2015-193501

(51) Int. Cl.
*G06F 19/00* (2018.01)
*G06F 17/30* (2006.01)
(Continued)

(52) U.S. Cl.
CPC ........ *G06F 19/321* (2013.01); *G06F 3/04817* (2013.01); *G06F 17/30244* (2013.01); *H04N 1/00442* (2013.01)

(58) Field of Classification Search
CPC ............... G06F 19/321; G06F 19/3443; G06F 19/3487; G06F 19/345; G06F 17/30244;
(Continued)

(56) References Cited

U.S. PATENT DOCUMENTS 7,130,457 B2 * 10/2006 Kaufman .............. G06F 19/321
382/128
7,162,066 B2 * 1/2007 Oosawa .................... G06T 5/50
378/205

(Continued)

FOREIGN PATENT DOCUMENTS

JP     2008-257292     10/2008
JP     2010-017410     1/2010

*Primary Examiner* — Michael Osinski
(74) *Attorney, Agent, or Firm* — Wenderoth, Lind & Ponack, L.L.P.

(57) ABSTRACT

A control method for an information terminal including a computer, the control method including controlling the computer to 1) detect whether information indicating a region of interest in a target medical image to be interpreted is input, 2) receive a plurality of similar medical images similar to the target medical image from a case search system, the received similar medical images including an axial image and a coronal image, and 3) display the axial image or the coronal image on a display such that the axial image is displayed when the number of regions of interest indicated by the information input to indicate region of interests is one while the coronal image is displayed when the number of regions of interest indicated by the information input to indicate region of interests is two or more or in a case where the information indicating regions of interest is not input.

11 Claims, 40 Drawing Sheets

(51) Int. Cl.
H04N 1/00 (2006.01)
G06F 3/0481 (2013.01)

(58) Field of Classification Search
CPC .............. G06F 17/30259; G06T 7/0012; G06T 2207/30004; G06T 2207/30061; A61B 5/416; A61B 5/7445; A61B 6/032; A61B 6/463; A61B 6/563; G06K 2209/05; G06K 9/00228; G06K 9/00369; G06K 9/3233

See application file for complete search history.

(56) References Cited

U.S. PATENT DOCUMENTS

| | | | |
|---|---|---|---|
| 7,346,199 B2* | 3/2008 | Pfaff | G06T 19/00 382/128 |
| 8,009,936 B2* | 8/2011 | Oosawa | G06F 17/30259 382/305 |
| 8,160,320 B2* | 4/2012 | Li | A61B 6/032 382/128 |
| 8,521,561 B2* | 8/2013 | Sasai | G06F 17/30265 705/2 |
| 8,730,234 B2* | 5/2014 | Iizuka | G06T 7/0012 128/922 |
| 8,799,013 B2* | 8/2014 | Gustafson | G16H 50/70 705/2 |
| 8,953,857 B2* | 2/2015 | Kondo | G06Q 50/22 382/128 |
| 9,008,390 B2* | 4/2015 | Takata | G06F 19/321 382/128 |
| 9,111,027 B2* | 8/2015 | Kozuka | G06Q 10/06 |
| 9,451,924 B2* | 9/2016 | Bernard | G06T 11/60 |
| 9,594,871 B2* | 3/2017 | Takata | G06F 19/322 |
| 2001/0043729 A1* | 11/2001 | Giger | G06F 19/321 382/128 |
| 2004/0003001 A1 | 1/2004 | Shimura | |
| 2004/0105574 A1* | 6/2004 | Pfaff | G06T 19/00 382/128 |
| 2007/0237377 A1 | 10/2007 | Oosawa | |
| 2008/0052126 A1* | 2/2008 | Sasai | G06F 17/30265 705/3 |
| 2008/0095418 A1* | 4/2008 | Moriya | A61B 6/563 382/128 |
| 2008/0240494 A1* | 10/2008 | Oosawa | G06F 17/30259 382/100 |
| 2008/0243395 A1 | 10/2008 | Oosawa et al. | |
| 2009/0080734 A1* | 3/2009 | Moriya | G06F 19/321 382/128 |
| 2009/0279753 A1* | 11/2009 | Sakaida | A61B 5/7435 382/128 |
| 2010/0228727 A1* | 9/2010 | Hisanaga | G06F 19/321 707/723 |
| 2010/0231605 A1* | 9/2010 | Moriya | G06F 19/321 345/619 |
| 2010/0232661 A1* | 9/2010 | Hisanaga | G06F 19/321 382/128 |
| 2011/0054295 A1* | 3/2011 | Masumoto | A61B 5/055 600/407 |
| 2012/0183191 A1 | 7/2012 | Nakamura | |
| 2013/0088512 A1* | 4/2013 | Suzuki | A61B 6/463 345/629 |
| 2015/0097869 A1* | 4/2015 | Oh | G06F 3/0406 345/635 |
| 2015/0110380 A1* | 4/2015 | Kobayashi | G06T 7/0014 382/132 |
| 2015/0173684 A1* | 6/2015 | Takata | A61B 5/055 600/425 |
| 2015/0317434 A1* | 11/2015 | Kondo | A61B 5/00 705/3 |
| 2015/0317452 A1* | 11/2015 | Kozuka | G06F 19/321 705/2 |
| 2015/0347464 A1* | 12/2015 | Takata | H01L 29/7835 707/728 |
| 2015/0356245 A1* | 12/2015 | Kozuka | G06F 19/321 705/2 |
| 2015/0356271 A1* | 12/2015 | Kozuka | G06F 19/3443 705/2 |
| 2016/0125162 A1* | 5/2016 | Takata | G06F 19/3443 705/2 |
| 2016/0128795 A1* | 5/2016 | Kozuka | A61B 6/03 715/771 |
| 2016/0247300 A1* | 8/2016 | Takata | G06F 17/30259 |
| 2017/0025158 A1* | 1/2017 | Miyake | G06F 19/345 |
| 2017/0090739 A1* | 3/2017 | Kozuka | G06F 3/0482 |
| 2017/0091413 A1* | 3/2017 | Kondo | G06F 19/321 |
| 2017/0091582 A1* | 3/2017 | Takata | A61B 5/055 |
| 2017/0308254 A1* | 10/2017 | Yokouchi | G06F 3/0484 |
| 2017/0311037 A1* | 10/2017 | Ohmura | H04N 21/4621 |
| 2017/0325771 A1* | 11/2017 | Tsunomori | A61B 6/5217 |

* cited by examiner

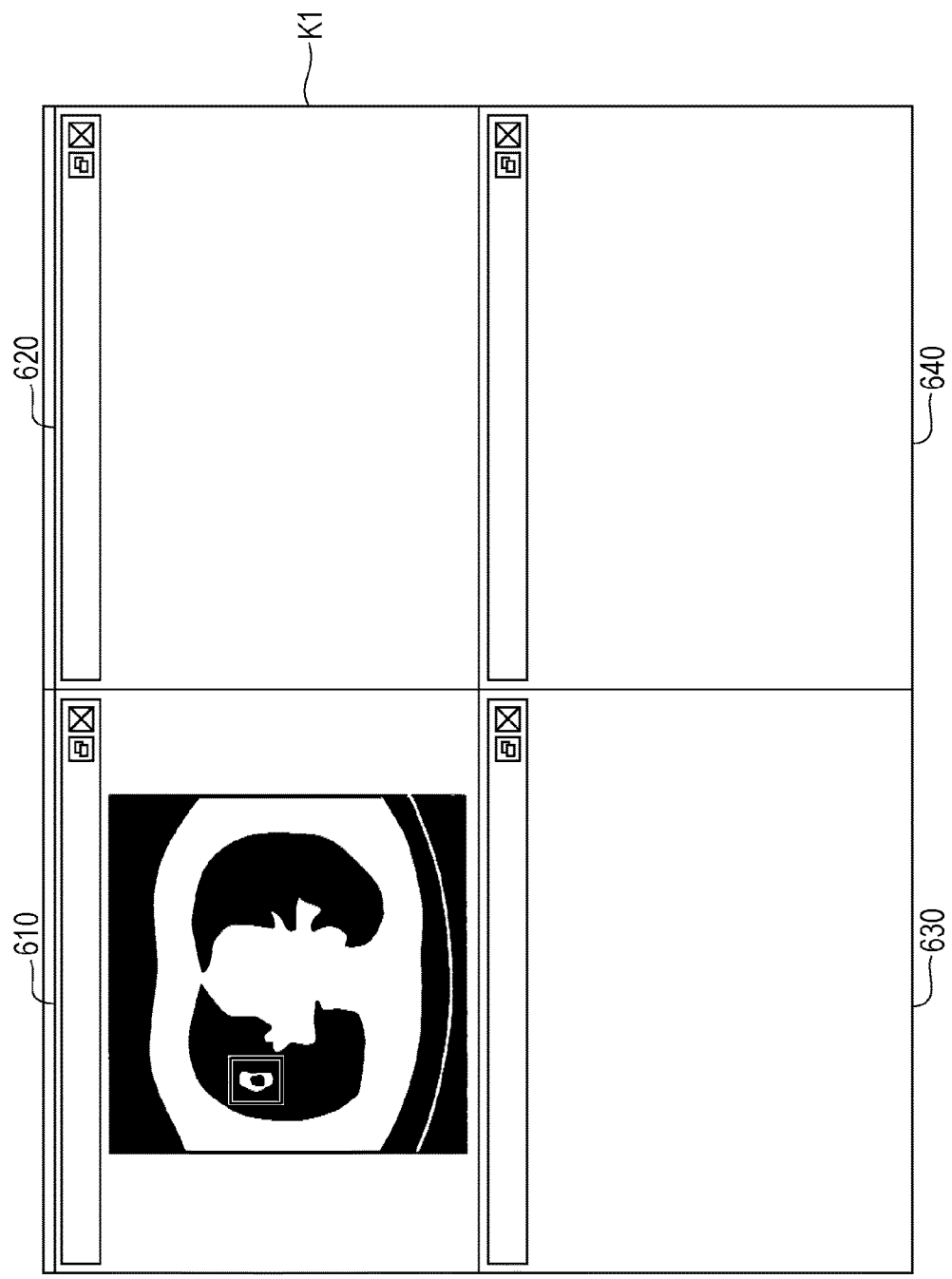

FIG. 6

| NAME-OF-DISEASE LIST | |
|---|---|
| 62 | ALL DISEASES |
| MYCOSIS | 14 |
| ASPERGILLOSIS | 8 |
| CRYPTOCOCCOSIS | 6 |
| NEOPLASTIC | 13 |
| PRIMARY LUNG CANCER | 10 |
| METASTATIC LUNG CANCER | 3 |
| NON-NEOPLASTIC | 6 |
| LUNG ABSCESS | 4 |
| INFLAMMATORY NODULE | 1 |

LESION DISTRIBUTION
☐ DIFFUSE  ☐ MULTIPLE
☒ SEGMENTAL  ☒ SUBPLEURAL
☐ BRONCHIAL  ☐ HEMATOGENOUS
☐ BILATERAL

— 713
— 714
— 730
— 750
— 710
— 715
— K2

Images (left to right, top to bottom):
- LUNG ABSCESS 0.05
- PRIMARY LUNG CANCER 0.15
- ASPERGILLOSIS 0.17
- CRYPTOCOCCOSIS 0.26
- LUNG ABSCESS 0.32
- PULMONARY TUBERCULOSIS 0.54
- METASTATIC LUNG CANCER 0.64
- ASPERGILLOSIS 0.73
- SEPTIC EMBOLISM 0.98
- ASPERGILLOSIS 1.05
- PRIMARY LUNG CANCER 1.42
- PRIMARY LUNG CANCER 1.51
- PRIMARY LUNG CANCER 1.76
- METASTATIC LUNG CANCER 2.97
- PRIMARY LUNG CANCER 3.44

FIG. 9

| NAME-OF-DISEASE LIST | 730 | |
|---|---|---|
| MYCOSIS | 14 | 731 |
|   ASPERGILLOSIS | 8 | 732 |
|   CRYPTOCOCCOSIS | 6 | 733 |
| NEOPLASTIC | 13 | 734 |
|   PRIMARY LUNG CANCER | 10 | 735 |
|   METASTATIC LUNG CANCER | 3 | 736 |
| NON-NEOPLASTIC | 6 | 737 |
|   LUNG ABSCESS | 4 | 738 |
|   SARCOIDOSIS | 1 | 739 |
|   SEPTIC EMBOLISM | 1 | 740 |
| MYCOBACTERIOSIS | 6 | 741 |
|   NON-TUBERCULOUS MYCOBACTERIOSIS | 4 | 742 |
|   PULMONARY TUBERCULOSIS | 2 | 743 |
| OTHERS | 2 | 744 |
|   BRONCHIECTASIS | 1 | 745 |
|   … | 1 | |

FIG. 11

| NAME-OF-DISEASE LIST | |
|---|---|
| MYCOSIS | 14 |
| ASPERGILLOSIS | 8 |
| CRYPTOCOCCOSIS | 6 |
| NEOPLASTIC | 13 |
| PRIMARY LUNG CANCER | 10 |
| METASTATIC LUNG CANCER | 3 |
| NON-NEOPLASTIC | 6 |
| LUNG ABSCESS | 4 |
| INFLAMMATORY NODULE | 1 |

LESION DISTRIBUTION
☐ DIFFUSE  ☐ MULTIPLE
☐ SEGMENTAL  ☒ SUBPLEURAL
☐ BRONCHIAL  ☐ HEMATOGENOUS
☐ BILATERAL

METASTATIC LUNG CANCER 0.64
METASTATIC LUNG CANCER 2.97
METASTATIC LUNG CANCER 6.44

FIG. 12

LESION DISTRIBUTION ⎯750
☐ DIFFUSE ⎯751    ☐ MULTIPLE ⎯755
▨ SEGMENTAL ⎯752  ☐ SUBPLEURAL ⎯756
☐ BRONCHIAL ⎯753  ☐ HEMATOGENOUS ⎯757
☐ BILATERAL ⎯754

FIG. 13

LESION DISTRIBUTION ⎯750
☐ DIFFUSE ⎯751    ☐ MULTIPLE ⎯755
▨ SEGMENTAL ⎯752  ☐ SUBPLEURAL ⎯756
☐ BRONCHIAL ⎯753  ☐ HEMATOGENOUS ⎯757
☑ BILATERAL ⎯754

| 1100 | PATIENT ID | 123456 |
|---|---|---|
| 1200 | NAME | TARO PANA |
| 1300 | AGE | 28 |
| 1400 | GENDER | MALE |
| 1500 | ANAMNESIS | NONE |
| 1600 | FAMILY HISTORY | NONE |
| 1700 | CHIEF COMPLAINT | COUGH |
| 1800 | EXAMINATION INFORMATION | (SHOWN IN FIG. 16) |
| 1900 | DEFINITIVE DIAGNOSIS | MYCOPLASMA PNEUMONIA |

FIG. 16

|  | | 1800 |
|---|---|---|
| 1810 | EXAMINATION ID | 13227895 |
| 1820 | EXAMINATION DATE/TIME | 2/5/20XX AT 10 |
| 1830 | EXAMINATION ITEM | BLOOD TEST |
| 1840 | RESULT OF EXAMINATION | YYYY1 |
|  | EXAMINATION ID | 13227903 |
|  | EXAMINATION DATE | 2/5/20XX AT 11 |
|  | EXAMINATION ITEM | SIMPLE X-RAY INSPECTION (CHEST) |
|  | RESULT OF EXAMINATION | YYYY2 |
|  | EXAMINATION ID | 13227989 |
|  | EXAMINATION DATE | 2/9/20XX AT 9 |
|  | EXAMINATION ITEM | CT (CHEST) |
|  | RESULT OF EXAMINATION | YYYY3 |

| 1810 | EXAMINATION ID | 13227989 |
|---|---|---|
| 3100 | OBSERVATION | MANY NODULES WITH A SIZE OF 0.5 cm TO 1 cm ARE OBSERVED IN RIGHT LUNG FIELD... |
| 3200 | DIAGNOSIS | SUSPECTED TO BE INFLAMMATORY NODULE OR PULMONARY TUBERCULOSIS. |

| | |
|---|---|
| 4100 — SIMILAR CASE ID | SIM5232 |
| 4200 — SLICE ID | CT149400025 |
| 4300 — AREA-OF-INTEREST INFORMATION | xl, yt, xr, yb |
| 4400 — IMAGE FEATURE DATA | f1, f2, f3, ..., fN |
| 4500 — THUMBNAIL IMAGE DATA | $(I_{0,0}, I_{0,1}, ..., I_{w-1, h-1})$ |
| 4600 — LESION DISTRIBUTION INFORMATION | |
| 4700 — DEFINITIVE DIAGNOSIS (BROADLY-CLASSIFIED DISEASE NAME) | NEOPLASTIC |
| 4800 — DEFINITIVE DIAGNOSIS (FINELY-CLASSIFIED DISEASE NAME) | PRIMARY LUNG CANCER |

| | |
|---|---|
| 4610 — DIFFUSE | 0 |
| 4620 — SEGMENTAL | 0 |
| 4630 — BRONCHIAL | 0 |
| 4640 — BILATERAL | 0 |
| 4650 — MULTIPLE | 0 |
| 4660 — SUBPLEURAL | 0 |
| 4670 — HEMATOGENOUS | 1 |

| 5100 | SIMILAR CASE ID | SIM10046 |
|---|---|---|
| 5200 | SLICE ID | CT149391 |
| 5300 | IMAGE FEATURE DATA | f1, f2, f3, ..., fN |
| 5400 | THUMBNAIL IMAGE DATA | $(I_{0,0}, I_{0,1}, I_{0,0}, ..., I_{w-1, h-1})$ |
| 5500 | DEFINITIVE DIAGNOSIS (BROADLY-CLASSIFIED DISEASE NAME) | PNEUMONIA |
| 5600 | DEFINITIVE DIAGNOSIS (FINELY-CLASSIFIED DISEASE NAME) | BACTERIAL PNEUMONIA |

FIG. 23

| PATIENT ID | NAME OF PATIENT | EXAMINATION DATE/TIME | EXAMINATION ID | EXAMINATION ITEM |
|---|---|---|---|---|
| 443982 | ICHIRO YAMADA | 12/1/20XX | 23982874 | MR (HEAD) |
| 123456 | TARO PANA | 5/8/20XX | 13227989 | CT (CHEST) |
| 345455 | ... | ... | ... | ... |
| 235982 | ... | ... | ... | ... |

800

| SERIES ID | DESCRIPTION | IMAGE |
|---|---|---|
|  |  |  |
|  |  |  |
|  |  |  |

| PATIENT ID | NAME OF PATIENT | EXAMINATION DATE/TIME | EXAMINATION ID | EXAMINATION ITEM |
|---|---|---|---|---|
| 443982 | ICHIRO YAMADA | 12/1/20XX | 23982874 | MR (HEAD) |
| 123456 | TARO PANA | 5/8/20XX | 13227989 | CT (CHEST) |
| 345455 | ... | ... | ... | ... |
| 235982 | ... | ... | ... | ... |

| SERIES ID | DESCRIPTION | IMAGE |
|---|---|---|
| CT152729 | LUNG FIELD CONDITION SLICE THICKNESS: 5 mm | |
| CT152730 | LUNG FIELD CONDITION SLICE THICKNESS: 1 mm | |
| CT152731 | MEDIASTINAL WINDOW SLICE THICKNESS: 5 mm | |

FIG. 31

| NAME-OF-DISEASE ID | BROADLY-CLASSIFIED DISEASE NAME | FINELY-CLASSIFIED DISEASE NAME | NUMBER | SIMILAR CASE ID |
|---|---|---|---|---|
| DIS528 | NEOPLASTIC | PRIMARY LUNG CANCER | 10 | SIM258, SIM551, SIM1209, SIM2341, ... |
| DIS922 | MYCOSIS | ASPERGILLOSIS | 8 | ... |
| ... | MYCOSIS | CRYPTOCOCCOSIS | 6 | ... |
| ... | NON-NEOPLASTIC | LUNG ABSCESS | 4 | ... |
| ... | MYCOBACTERIOSIS | NON-TUBERCULOUS MYCOBACTERIOSIS | 4 | ... |
| ... | ... | ... | ... | ... |

FIG. 32

| NAME-OF-DISEASE LIST | 730 |
|---|---|
| PRIMARY LUNG CANCER | 10 |
| ASPERGILLOSIS | 8 |
| CRYPTOCOCCOSIS | 6 |
| LUNG ABSCESS | 4 |
| NON-TUBERCULOUS MYCOBACTERIOSIS | 4 |
| METASTATIC LUNG CANCER | 3 |
| PULMONARY TUBERCULOSIS | 2 |
| INFLAMMATORY NODULE | 1 |
| SEPTIC EMBOLISM | 1 |
| BRONCHIECTASIS | 1 |
| UNIDENTIFIED | 1 |

FIG. 33

| NAME-OF-DISEASE LIST | 730 |
|---|---|
| MYCOSIS | 14 |
| NEOPLASTIC | 13 |
| NON-NEOPLASTIC | 6 |
| MYCOBACTERIOSIS | 6 |
| OTHERS | 2 |

FIG. 34

| NAME-OF-DISEASE LIST | 730 |
|---|---|
| MYCOSIS | 14 |
|   ASPERGILLOSIS | 8 |
|   CRYPTOCOCCOSIS | 6 |
| NEOPLASTIC | 13 |
|   PRIMARY LUNG CANCER | 10 |
|   METASTATIC LUNG CANCER | 3 |
| NON-NEOPLASTIC | 6 |
|   LUNG ABSCESS | 4 |
|   SARCOIDOSIS | 1 |
|   SEPTIC EMBOLISM | 1 |
| MYCOBACTERIOSIS | 6 |
|   NON-TUBERCULOUS MYCOBACTERIOSIS | 4 |
|   PULMONARY TUBERCULOSIS | 2 |
| OTHERS | 2 |
|   BRONCHIECTASIS | 1 |
|   ... | 1 |

| DISTRIBUTION NAME | NUMBER OF CASES | SIMILAR CASE ID |
|---|---|---|
| DIFFUSE | 3 | SIM2521, SIM4123, SIM5225 |
| SEGMENTAL | 0 | NONE |
| BRONCHIAL | 2 | SIM0006, SIM1892, SIM4399 |
| BILATERAL | 12 | ... |
| MULTIPLE | 22 | ... |
| SUBPLEURAL | 0 | NONE |
| HEMATOGENOUS | 5 | ... |

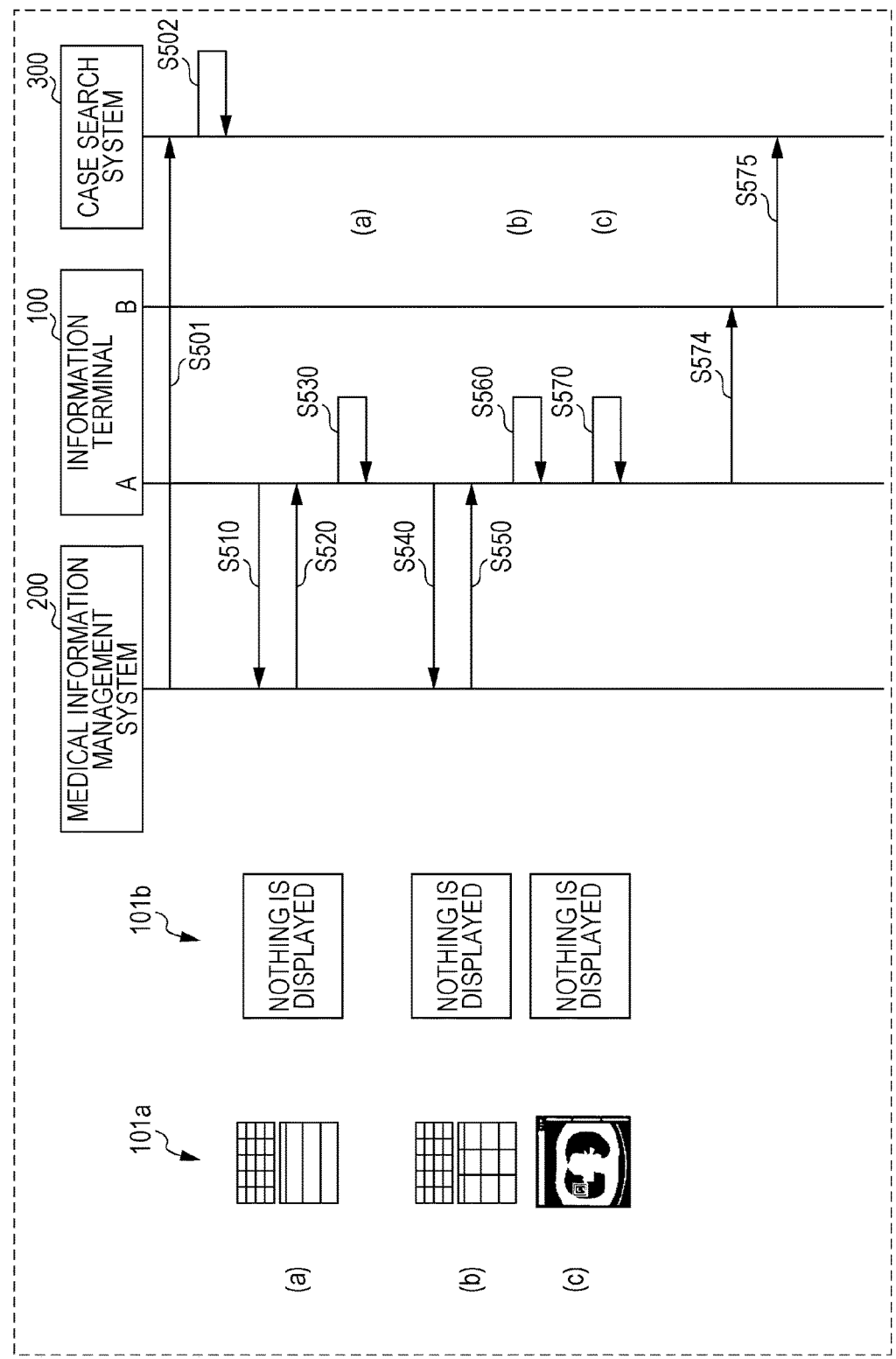

CONTROL METHOD AND STORAGE MEDIUM FOR SEARCHING MEDICAL IMAGES SIMILAR TO A TARGET IMAGE

BACKGROUND

1. Technical Field

The present disclosure relate to a method of controlling an information terminal for searching for a similar medical image similar to a medical image to be interpreted, and to a storage medium.

2. Description of the Related Art

In recent years, advance in medical imaging apparatuses such as a computed tomography (CT) apparatus, a magnetic resonance imaging (MRI) apparatus has been achieved, and they are now widely used. With these medical imaging apparatuses such as the CT apparatus, the MRI apparatus, and the like, it is possible to acquire a large number of digital high-resolution medical images. Medical images interpreted by doctors are being accumulated together with their interpretation reports in a picture archiving and communication systems (PACS). For example, as disclosed in Japanese Unexamined Patent Application Publication No. 2008-257292, to obtain information useful in interpreting a target medical image to be interpreted, a technique is under development to search for a past medical image similar to the target medical image to be interpreted from past cases accumulated in the PACS.

SUMMARY

One non-limiting and exemplary embodiment provides a technique to improve the method of controlling an information terminal for searching for a similar medical image similar to a medical image to be interpreted.

In one general aspect, the techniques disclosed here feature a control method for an information terminal including a computer, the control method including controlling the computer to detect whether information indicating a region of interest in a target medical image to be interpreted is input, controlling the computer to receive a plurality of similar medical images similar, with a similarity level equal to or higher than a predetermined level, to the target medical image from a case search system, the received similar medical images including an axial image and a coronal image, controlling the computer to display the axial image or the coronal image on a display such that the axial image is displayed in a case where the number of regions of interest indicated by the information input to indicate region of interests is one while the coronal image is displayed in a case where the number of regions of interest indicated by the information input to indicate region of interests is two or more or in a case where the information indicating regions of interest is not input.

It should be noted that general or specific embodiments may be implemented as a system, a method, an integrated circuit, a computer program, a storage medium, or any selective combination thereof.

The computer-readable storage medium may be a non-transitory storage medium such as a compact disc-read only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 5 is a diagram illustrating an example of a basic screen that is to be displayed on a display immediately after a similar case search application is started on an information terminal;

FIG. 6 is a diagram illustrating an example of a basic screen that is to be displayed on a display immediately after a similar case search application is started on an information terminal in a situation in which one region of interest is set in a search query image;

FIG. 9 is a diagram illustrating, in an enlarged manner, a name-of-disease list display area;

FIG. 11 is a diagram illustrating a basic screen displayed when similar cases are narrowed by "metastatic lung cancer";

FIG. 12 is a diagram illustrating, in an enlarged manner, a distribution type list display area;

FIG. 13 is a diagram illustrating a distribution type list display area in which a check box of "bilateral" is checked;

FIG. 15 is a diagram illustrating a data structure of patient information;

FIG. 16 is a diagram illustrating a data structure of medical examination information registered in the patient information shown in FIG. 15;

FIG. 18 is a diagram illustrating a data structure of a diagnosis report;

FIG. 19 is a diagram illustrating a data structure of similar case data of localized lesion;

FIG. 20 is a diagram illustrating a data structure of similar case data of diffuse lesion;

FIG. 23 is a diagram illustrating a screen of a list of examinations;

FIG. 24 is a diagram illustrating a screen of a list of examinations displayed after an examination is selected;

FIG. 31 is a diagram illustrating a data structure of a name-of-disease list generated in S1300 in FIG. 30;

FIG. 32 is a diagram illustrating a first example of a manner of displaying a name-of-disease list display area;

FIG. 33 is a diagram illustrating a second example of a manner of displaying a name-of-disease list display area;

FIG. 34 is a diagram illustrating a third example of a manner of displaying of a name-of-disease list display area;

FIG. 45 is a sequence diagram illustrating an example different from that shown in FIG. 44.

DETAILED DESCRIPTION

Figure 1:
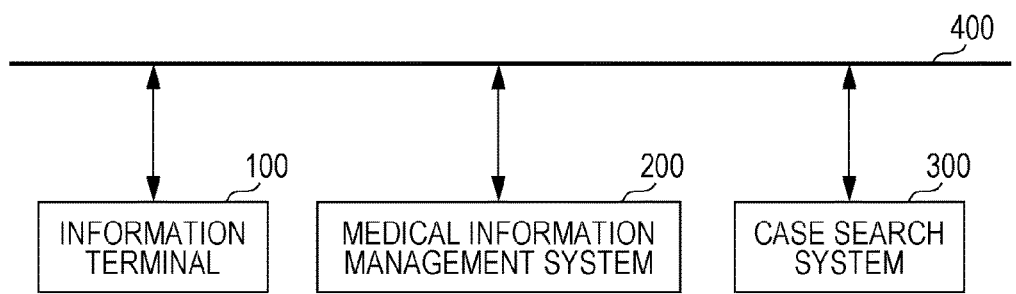
FIG. 1 is diagram illustrating an overall configuration of a hospital information system using an information terminal according to an embodiment.

Underlying Knowledge Forming Basis of the Present Disclosure

First, a basic idea of embodiments of the present disclosure is described below.

Japanese Unexamined Patent Application Publication No. 2008-257292 discloses an image diagnosis support apparatus that presents a case image, or statistical information associated with a disease, useful for determining the disease in image diagnosis based on a target image to be diagnosed. In this image diagnosis support apparatus, a target image to be diagnosed and information on typical cases of each disease are displayed on a search result screen. More specifically, information displayed on the search result screen includes i) image of a typical case of each of top-three diseases A, D, and G, ii) similarity level to the target image to be diagnosed, the number of registered cases, and the number of typical cases, for each of diseases, iii) the number of hits (total number of retrieved diseases), and iv) soft button "Next Page" for displaying information on other diseases that are not displayed on the current page (see paragraphs [0062] and [0063] and FIG. 6(E) in Japanese Unexamined Patent Application Publication No. 2008-257292).

However, Japanese Unexamined Patent Application Publication No. 2008-257292 includes no description at all about changing a manner of displaying an image of typical case for each disease on the search result screen. That is, Japanese Unexamined Patent Application Publication No. 2008-257292 does not discloses even a method of changing a manner of displaying an image of a typical case for each disease. More specifically, for example, no description is given as to a method of displaying an image of a typical case for each disease in the form of an axial image or a coronal image depending on a situation.

Through the consideration describe above, the inventors have got ideas of respective embodiments of the present disclosure described below.

In an aspect, the present disclosure provides a control method for an information terminal including a computer, the control method including controlling the computer to detect whether information indicating a region of interest in a target medical image to be interpreted is input, controlling the computer to receive a plurality of similar medical images similar, with a similarity level equal to or higher than a predetermined level, to the target medical image from a case search system, the plurality of received similar medical images including an axial image and a coronal image, and controlling the computer to display the axial image or the coronal image on a display such that the axial image is displayed in a case where the number of regions of interest indicated by the information input to indicate region of interests is one while the coronal image is displayed in a case where the number of regions of interest indicated by the information input to indicate region of interests is two or more or in a case where the information indicating regions of interest is not input.

In the present aspect, a plurality of similar medical images which are similar, with a similarity level equal to or higher than the predetermined similarity level, to a target medical image are received from the case search system, and the received similar medical images are displayed on the display. This makes it possible to extract similar medical images, which are to be useful in determining a name of disease of a lesion appearing in the target medical image, from a huge number of medical images registered in a medical image database and present the extracted similar medical images to a doctor.

Lesions may be in one of two distribution forms: a diffuse lesion; and a localized lesion. In the diffuse lesion, a lesion extends over a wide range of a whole internal organ. In contrast, in the localized lesion, a lesion locally extends in a part of an internal organ.

In the case of the diffuse lesion, the size of the area in which the lesion extends is very important information in identifying the name of disease. For example, in the case of medical images of lung, information as to whether the lesion extends to an upper lobe, a middle lobe, or a lower lobe of the lung is very useful information in identifying the name of disease. Therefore, in the similar case search system, when a similar medical image associated with the diffuse lesion is displayed on the display, it may be desirable to display a coronal image to make it possible to see the whole of the lesion at a glance.

On the other hand, in the localized lesion, information as to where a lesion extends in a direction along a blood vessel (for example, in the case of a lung, a blood vessel and a respiratory tract) and information regarding a three-dimensional shape of the lesion are very important two pieces of information in identifying the name of disease. Therefore, in the similar case search system, when a similar medical image associated with a localized lesion is displayed on the display, it may be desirable to display an axial image that allows it to determine whether the lesion extends in a direction along a blood vessel and to determine the three-dimensional shape of the lesion.

The determination as to whether a target medical image indicates a localized lesion or a diffuse lesion can be made based on whether designation information indicating a region of interest in the target medical image is input or note and based on the number of regions of interest indicated by the input designation information. This is because a region of interest designated by a doctor is a lesion included in a target medical image, and thus when the designation information indicates one region of interest, this suggests that the lesion is localized lesion. On the other hand, when the designation information indicates two or more regions of interest, the lesion extends in a large area, and thus it can be concluded that the lesion is a diffuse lesion. In a case where one lesion extends over a large area, there is possibility that a doctor does not input designation information indicating a region of interest. Therefore, when designation information is not input, it can be determined that the lesion is a diffuse lesion.

In the present aspect, when a plurality of similar medical images are displayed on the display, if the designation information indicates one region of interest, an axial image is used, but if the designation information indicates two or more region of interest or if no designation information is input, a coronal image is used. That is, in the case where the designation information indicates one region of interest, there is a high probability that a doctor wants to see a similar medical image of a localized lesion. Therefore, an axial image is displayed on the display. On the other hand, in the case where the designation information indicates two or more regions of interest or in the case where no designation information is input, there is a high probability that a doctor wants to see a similar medical image of a diffuse lesion. Therefore, a coronal image is displayed on the display. Thus, it is possible to effectively and efficiently present a similar medical image, which is information necessary in identifying a name of disease, to a doctor. In the aspect described above, in a case where the number of regions of interest indicated by the input information is one, the similarity level between the region of interest of the target medical image and a region of interest of each of the medical images may be equal to or higher than the predetermined similarity level, while in the case where the input information indicating the region of interesting indicates two or more regions of interest or in the case where no information indicating the region of interest is input, the similarity level between a set of images including the target medical image and a set of images including the medical images may be equal to or higher than the predetermined similarity level. In the aspect described above, the axial image may be an image taken along a cross section of a subject such that the cross section is perpendicular to a longitudinal axis of the subject, while the coronal image may be an image taken along a cross section of a subject such that the cross section is within a range of angle from 0° to 45° with respect to the longitudinal axis of the subject.

In the aspect described above, each of the similar medical images may be one of medical images included in a set of images taken by a tomographic imaging method and arranged in a first direction, and the axial image may be a medical image that is included in the set of images and that is the greatest of all images in terms of an area size of an area corresponding to the region of interest.

In this aspect, of axial images, an axial image that is the greatest in terms of the area size of an area corresponding to the region of interest is displayed on the display. That is, similar medical images are displayed for respective cases on the display such that a medical image corresponding to a greatest lesion size is selected from the set of images of each case and the selected medical image is displayed. Note that displaying the similar medical image with the greatest lesion size allows it to present a medical image best representing a feature of the lesion. That is, in the present aspect, the medical image best representing the feature of the lesion is presented, and this makes it possible for a doctor to more accurately make diagnosis.

In the aspect described above, for example, each of the similar medical images may be one of medical images included in a set of images taken by a tomographic imaging method and arranged in a first direction, and, in a case where information indicating the region of interest is input, the coronal image may be a medical image that is included in the set of images and that is the greatest of all images in terms of an area size of an area corresponding to the region of interest.

In the present aspect, of coronal images, a coronal image having the greatest total area size of a plurality of regions of interest is displayed on the display. That is, similar medical images are displayed for respective cases on the display such that a medical image corresponding to a greatest lesion size is selected from the set of images of each case and the selected medical image is displayed. Note that displaying the similar medical image with the greatest lesion size allows it to present a medical image best representing a feature of the lesion. That is, in the present aspect, the medical image best representing the feature of the lesion is presented, and this makes it possible for a doctor to more accurately make diagnosis.

In another aspect, the present disclosure provides a control method for an information terminal including a computer, the control method including controlling the computer to detect information indicating a region of interest in a target medical image to be interpreted, controlling the computer to receive similar medical images from a case search system, each of the similar medical images selected based on the target medical image, the received similar medical images including an axial image and a coronal image, and controlling the computer to display the axial image or the coronal image on a display such that the axial image is displayed in a case where the ratio of a size of the region of interest to a total size of the target medical image is smaller than a predetermined threshold value while the coronal image is displayed in a case where the ratio is equal to or greater than the threshold value.

In the present aspect, a plurality of similar medical images which are similar, with a similarity level equal to or higher than the predetermined similarity level, to a target medical image are received from the case search system, and the received similar medical images are displayed on the display. This makes it possible to extract similar medical images, which are to be useful in determining a name of disease of a lesion appearing in the target medical image, from a huge number of medical images registered in a medical image database and present the extracted similar medical images to a doctor.

Lesions may be in one of two distribution forms: a diffuse lesion and a localized lesion. In the localized lesion, the lesion locally extends in a part of an internal organ. On the other hand, in the case of the diffuse lesion, the lesion extends over a wide range of a whole internal organ.

In the diffuse lesion, the size of the area over which the lesion extends is very important information in identifying the name of disease. For example, in the case of medical images of lung, information as to whether the lesion extends to upper lobe, middle lobe, or lower lobe of the lung is very useful information in identifying the name of disease. Therefore, in the similar case search system, when a similar medical image associated with the diffuse lesion is displayed on the display, it may be desirable to display coronal images to make it possible to see the whole of the lesion at a glance.

In contrast, in the localized lesion, information as to where a lesion extends in a direction along a blood vessel (for example, in the case of a lung, a blood vessel and a respiratory tract) and information regarding a three-dimensional shape of the lesion are very important two pieces of information in identifying the name of disease. Therefore, in the similar case search system, when a similar medical image associated with a localized lesion is displayed on the display, it may be desirable to display an axial image that allows it to determine whether the lesion extends in a direction along a blood vessel and to determine the three-dimensional shape of the lesion.

The determination as to whether the target medical image represents a localized lesion or a diffuse lesion may be performed based on the ratio of the size of the region of interest in the target medical image to the total size of the target medical image. That is, the region of interest designated by a doctor is a lesion included in the target medical image, and thus, for example, when the ratio of the size of the region of interest to the total size of the target medical image is smaller than a predetermined threshold value, it can be concluded that the lesion is a localized lesion that is located at one location in an internal organ. On the other hand, for example, when the ratio of the size of the region of interest to the total size of the target medical image is equal to or greater than the predetermined threshold value, it can be concluded that the lesion is a diffuse lesion extending over a whole internal organ.

The ratio of the size of the region of interest to the total size of the target medical image may be represented by the ratio of the area size of the region of interest to the total area size of an internal organ included in the target medical image. When a region of interest is set, in many cases, a rectangle is used to designate the region of interest. In this case, an area other than an internal organ may be included in the region of interest. In view of the above, the ratio of the region of interest to the target medical image may be given by the ratio of the area size of an overlapping area between the region of interest and the internal organ to the area size of the area of the internal organ included in the target medical image. However, the calculation is easier for the case where simply region of interest is employed than for the case where the overlapping area between the region of interest and the internal organ is employed.

In the present aspect, when a plurality of similar medical images are displayed on the display, the axial image is displayed in a case where the ratio of a size of the region of interest to the total size of the target medical image is smaller than a predetermined threshold value while the coronal image is displayed in a case where the ratio is equal to or greater than the threshold value. That is, in the case where the ratio is smaller than the predetermined threshold value, similar medical images that a doctor wants to see are very likely to be of localized lesion. Therefore, axial images are displayed on the display. On the other hand, in the case where the ratio is equal or larger than the predetermined threshold value, similar medical images that a doctor wants to see are very likely to be of diffuse lesion. Therefore, coronal images are displayed on the display. Thus, it is possible to effectively and efficiently present similar medical images as information necessary in identifying a name of disease to a doctor.

In the aspect described above, for example, the target medical image may be a medical image of a lung captured using a tomographic imaging method, the ratio described above may be a ratio of an area size of an overlapping area between the region of interest and the lung to an area size of an area of the lung included in the target medical image, and the threshold value described above may be ¼.

Experimentally, when the ratio of the area size of the overlapping area between the region of interest and the lung to the area size of the area of the lung included in the target medical image is smaller than ¼, the lesion is a localized lesion, while when the ratio is equal to or larger than ¼, the lesion is a diffuse lesion. In the present aspect, when the ratio of the area size of the overlapping area between the region of interest and the lung to the area size of the area of the lung included in the target medical image is smaller than ¼, an axial image is used, while when the ratio is equal to or larger than ¼, a coronal image is used. Thus, it is possible to effectively and efficiently present to a doctor a similar medical image which is information necessary in identifying a name of disease.

In the control method for the information terminal including the computer according to the aspect described above, for example, the control method may further include controlling the computer to calculate the ratio based on the target medical image and the region of interest indicated by the input information indicating the region of interest.

In the control method for the information terminal including the computer according to the aspect described above, for example, the control method may further include controlling the computer to transmit the target medical image and the input information indicating the region of interest to the case search system, and receiving the ratio from the case search system.

In the control method for the information terminal including the computer according to the aspect described above, for example, the control method may further include controlling the computer to transmit information indicating a feature value of the region of interest to the case search system, and receiving the feature value of the region of interest and a plurality of similar medical images with a similarity level equal to or higher than the predetermined degree of similarity.

In the control method for the information terminal including the computer according to the aspect described above, for example, the control method may further include controlling the computer to transmit the target medical image and information indicating the region of interest to the case search system, and controlling the computer to receive a feature value of the region of interest and a plurality of similar medical images with a similarity level equal to or higher than the predetermined degree of similarity, the feature value and the similar medical images being obtained based on the target medical image and the information indicating the region of interest.

In an aspect, the present disclosure provides a control method for an apparatus including a processor to execute a process, the process including: receiving one or more regions of interest in a target medical image to be interpreted, each of the one or more regions of interest being a continuous area; outputting a first thumbnail image to be displayed on a display or a second thumbnail image to be displayed on the display, the first thumbnail image being provided based on an axial image, the second thumbnail image being provided based on an coronal image, the first thumbnail image being outputted if a total number of the one or more regions of interest is one, and the second thumbnail image being outputted if the total number of the one or more regions of interest is two or more. In the aspect described above, a similarity level between the region of interest and a region of interest of the axial image may be equal to or higher than a predetermined level, a similarity level between a first set of images including the target medical image and a second set of images including the coronal image may be equal to or higher than a predetermined level, and the first set of images may be obtained through one medical examination performed on a first subject and the second set of images may be obtained through one medical examination performed on a second subject. In the aspect described above, the axial image may be an image taken along a first cross section of a third subject and the first cross section may be perpendicular to a longitudinal axis of the third subject, and the coronal image may be an image taken along a second cross section of the second subject and the second cross section may be within a range of angle from 0° to 45° with respect to the longitudinal axis of the second subject.

Embodiments

Embodiments of the present disclosure are described below with reference to drawings. Note that similar constituent elements are denoted by similar reference symbols or numerals over all drawings.

Overall Configuration

FIG. 1 is diagram illustrating an overall configuration of a hospital information system using an information terminal according to an embodiment. As illustrated in FIG. 1, the hospital information system includes an information terminal 100, a medical information management system 200, and a case search system 300.

The information terminal 100, the medical information management system 200, and the case search system 300 are connected to each other via a network 400 such that they are allowed to communicate with each other.

Note that the medical information management system 200 and the case search system 300 do not necessarily need to be installed inside a hospital, but they may be software installed outside the hospital, for example, in a data center, a private cloud server, a public cloud server, or the like. In a case where the medical information management system 200 and the case search system 300 are installed inside a hospital, a local area network may be used as the network 400. As for the local area network, a wired LAN according to the IEEE802.3 series, a wireless LAN according to the IEEE802.11 series, or a combination thereof may be employed. In a case where the medical information management system 200 and the case search system 300 are realized using a server installed outside a hospital, the Internet may be employed as the network 400.

As for the information terminal 100, an information terminal such as a personal computer, a tablet terminal, or the like may be employed. As for the medical information management system 200, a picture archiving and communication system (PACS), an electronic medical record system, or the like may be employed.

Information Terminal 100

Figure 2:
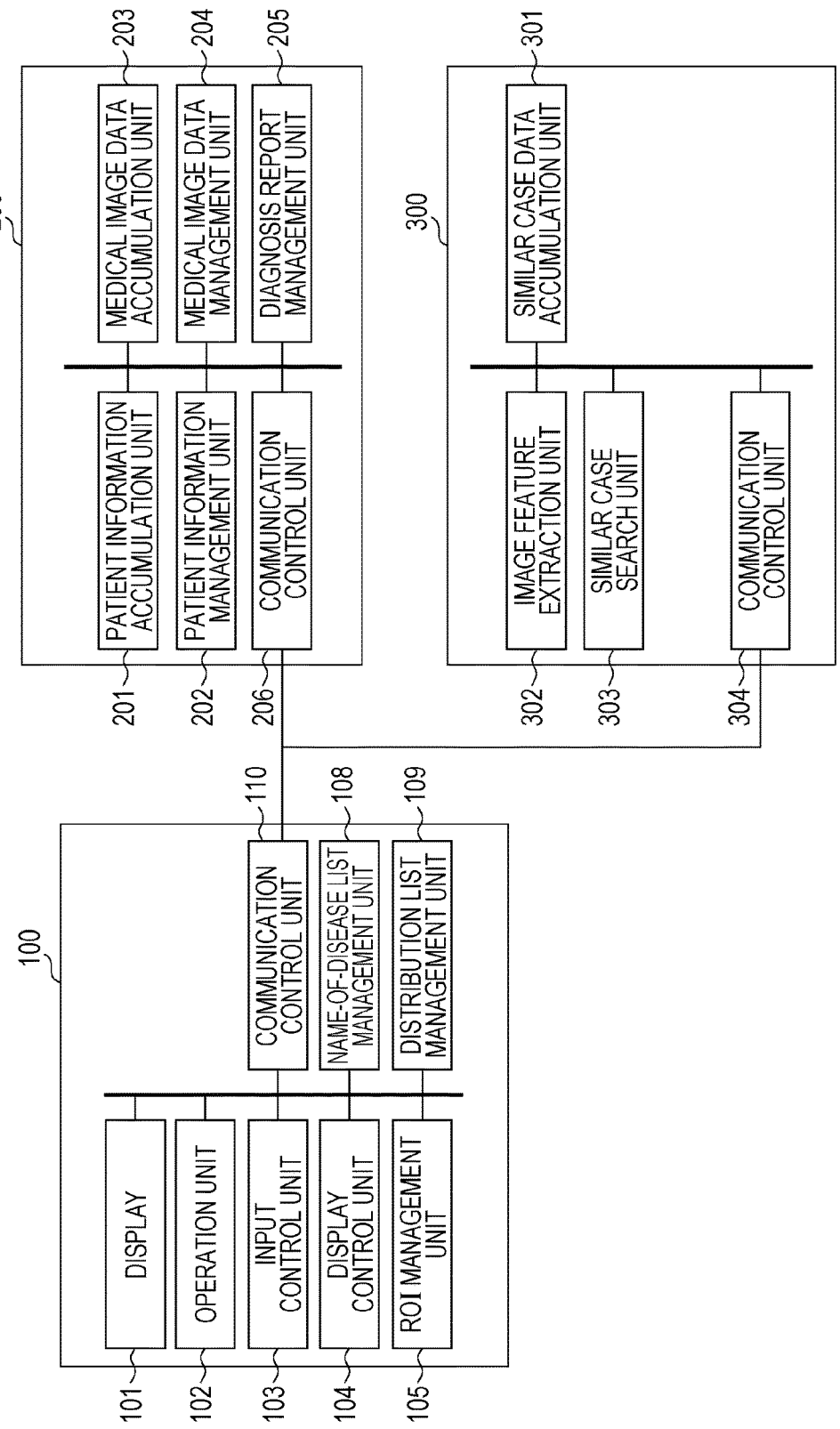
FIG. 2 is a block diagram illustrating configurations of an information terminal, a medical information management system, and a case search system.

FIG. 2 is a block diagram illustrating configurations of the information terminal 100, the medical information management system 200, and the case search system 300. As shown in FIG. 2, the information terminal 100 includes a display 101, an operation unit 102, an input control unit 103, a display control unit 104, a ROI management unit 105, a name-of-disease management unit 108, a distribution type list management unit 109, and a communication control unit 110.

The display 101 is realized using, for example, a liquid crystal monitor, and the display 101 displays a medical image used in diagnosis, a medical record image, a report input image for describing a diagnosis result, and the like. Note that at least one display 101 is necessary, and two or three displays 101 are used in image diagnosis in many cases. In the present embodiment, two displays 101 are used. Hereinafter, one of the two displays 101 is referred to as a display 101a, and the other one is referred to as a display 101b (see FIG. 3).

Figure 3:
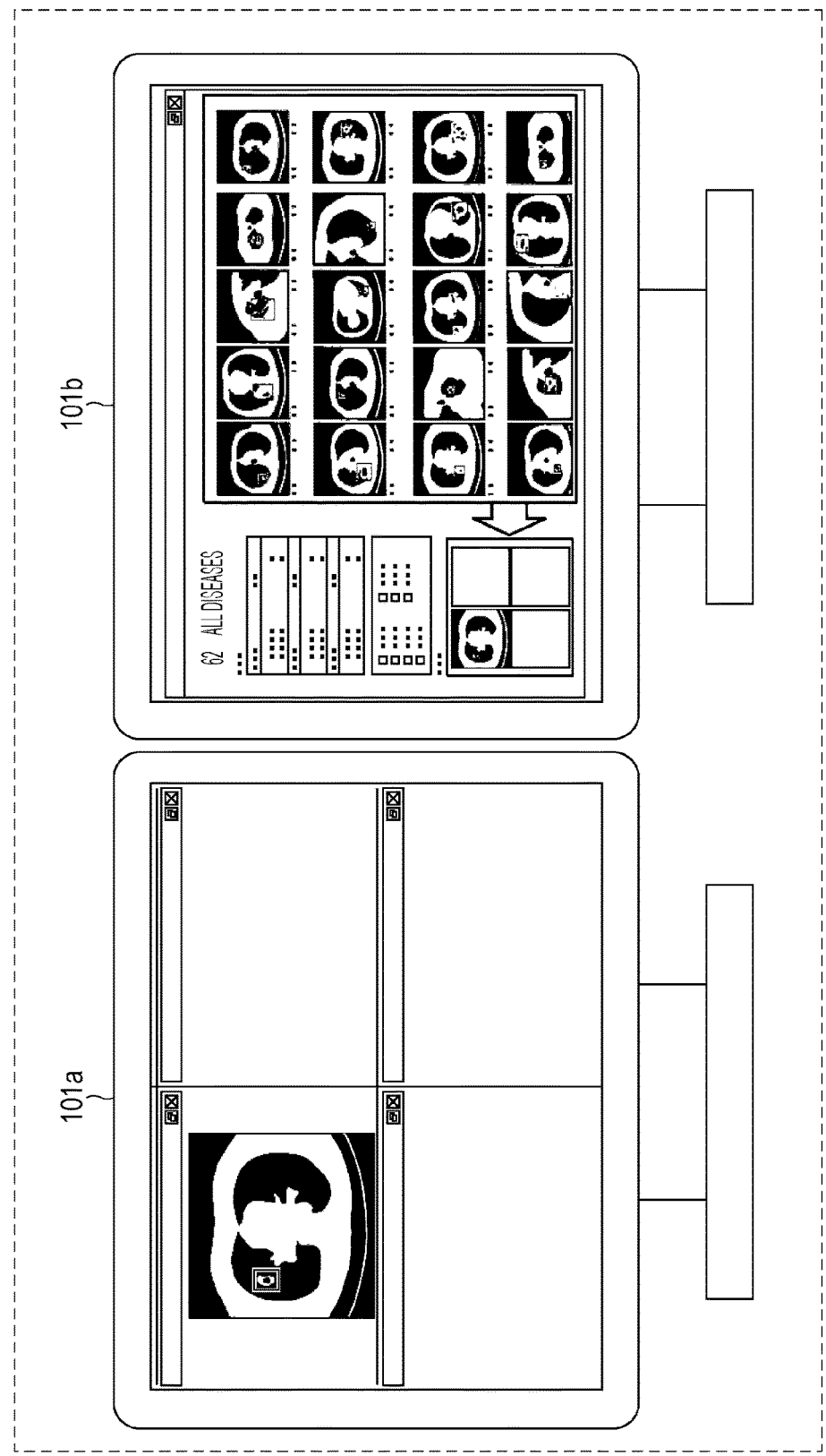
FIG. 3 is a diagram illustrating external appearances of two displays.

FIG. 3 illustrates external appearances of the two displays 101a and 101b. In FIG. 3, on the display 101a, four medical image viewers are displayed in an array including two rows and two columns, while the screen of the case search system 300 is displayed on the display 101b. In the case where only one display 101 is used, two display screens are displayed in different areas on the single display 101.

The operation unit 102 includes, for example, a keyboard and a mouse, and the operation unit 102 accepts various operations performed by a user to give inputs to the information terminal 100. More specifically, for example, the operation unit 102 receives an operation performed by a user on a medical image and a medical record image displayed on the display 101, and also receives an operation of inputting a diagnosis result on the report input screen.

When the input control unit 103 detects a user operation on the operation unit 102, the input control unit 103 interprets a content of the operation and notifies other constituent units of the content of the operation. More specifically, for example, the input control unit 103 detects a location where a mouse pointer is to be located on the display 101, from coordinate data output from a mouse used as an element of the operation unit 102, and displays the mouse pointer on the display 101. When the input control unit 103 detects clicking on the mouse, if a GUI (Graphical User Interface) element such as a GUI button generated by the display control unit 104 is displayed at the location where the mouse pointer is displayed, then the input control unit 103 determines that the GUI is selected by a user, and the input control unit 103 notifies other constituent units that the GUI element is selected by the user.

The display control unit 104 generates a GUI of the information terminal 100 and displays it on the display 101.

When similar case search is performed, the ROI management unit 105 generates region-of-interest information indicating a region of interest set in a search query image described later, and stores the region-of-interest information in a memory and manages it.

The name-of-disease management unit 108 generates a name-of-disease list (FIG. 9) of similar cases displayed in a case display area 710 (FIG. 6), and stores the generated name-of-disease list in a memory and manages it.

The distribution type list management unit 109 generates a distribution type list (FIG. 12) indicating a lesion distribution of a similar case displayed in the case display area 710, and stores the generated distribution type list in a memory and manages it.

The communication control unit 110 includes, for example, a communication apparatus for connecting the information terminal 100 to the network 400, and controls communication between the information terminal 100 and the medical information management system 200 and communication between the information terminal 100 and case search system 300. The communication control unit 110 accepts transmission requests of various kinds of data from other blocks, and transmits the data to the medical information management system 200 or the case search system 300. The communication control unit 110 receives data transmitted from the medical information management system 200 or the case search system 300 and transfers the data to a proper block.

Medical Information Management System 200

As shown in FIG. 2, the medical information management system 200 includes a patient information accumulation unit 201, a patient information management unit 202, a medical image data accumulation unit 203, a medical image data management unit 204, a diagnosis report management unit 205, and a communication control unit 206.

The patient information accumulation unit 201 accumulates patient information 1000 (FIG. 15) in terms of personal information such as gender, age, and the like of a patient, clinical information such as an anamnesis, and medical examination information in terms of blood test and the like.

The patient information management unit 202 performs, to manage the patient information 1000, a process including registering data input by a user into the patient information 1000 (FIG. 15) accumulated in the patient information accumulation unit 201 so as to update the patient information 1000, and outputting the patient information 1000 to the display control unit 104. The medical image data accumulation unit 203 accumulates medical image data in terms of examination images of patients.

The medical image data management unit 204 accumulates medical image data in the medical image data accumulation unit 203 and manages the medical image data.

The diagnosis report management unit 205 manages a diagnosis report 3000 (FIG. 18) describing diagnosis results given by doctors on examinations on patients.

The communication control unit 206 includes, for example, a communication apparatus for connecting the medical information management system 200 to the network 400. The communication control unit 206 accepts transmission requests of various kinds of data from other blocks, and transmits the data to the information terminal 100 or the case search system 300. The communication control unit 206 receives data transmitted from the information terminal 100 or the case search system 300 and transfers the data to a proper block.

Case Search System 300

As shown in FIG. 2, the case search system 300 includes a similar case data accumulation unit 301, an image feature extraction unit 302, a similar case search unit 303 and a communication control unit 304.

Of various kinds of similar cases managed by the medical information management system 200, particular data described below is accumulated in advance by the similar case data accumulation unit 301. That is, the similar case data accumulation unit 301 accumulates image features extracted from many similar cases selected as data of similar cases to be subjected to searching, similar case data 4000 (FIG. 19) associated with localized lesion including generated thumbnail images or the like, and similar case data 5000 (FIG. 20) associated with diffuse lesion.

The image feature extraction unit 302 extracts an image feature of an area (region of interest) identified by region-of-interest information of a search query image transmitted from the communication control unit 110 of the information terminal 100 (in a case where the number of regions of interest is equal to one), or the image feature extraction unit 302 extracts an image feature of a series image transmitted from the communication control unit 110 of the information terminal 100 (in a case where no region of interest is set (that is, the number of regions of interest is equal to zero) or the number of region of interests is equal to or larger than two, or, in a modified embodiment, the area ratio of a region of interest is equal to or greater than a predetermined value). Note that the region-of-interest information is an example of designation information indicating a region of interest.

In the present embodiment, the extracted content of the image feature is changed depending on the number of regions of interest specified by a user. That is, in the case where the number of regions of interest indicated by the region-of-interest information is equal to one, the image feature extraction unit 302 extracts a plurality of kinds (with a plurality of dimensions) of image features predetermined for localized lesions. On the other hand, in the case where the number of regions of interest indicated by the region-of-interest information is equal to or greater than two and in the case where the region-of-interest information includes no region of interest, the image feature extraction unit 302 extracts a plurality of kinds (with a plurality of dimensions) of image features predetermined for diffuse lesions.

The similar case search unit 303 generates a similar case search result by comparing the image feature extracted by the image feature extraction unit 302 with one or more image features of similar cases accumulated in the similar case data accumulation unit 301.

The communication control unit 304 includes, for example, a communication apparatus for connecting the case search system 300 to the network 400. The communication control unit 304 accepts transmission requests of various kinds of data from other blocks and transmits the requested data to the information terminal 100 or the medical information management system 200. The communication control unit 304 receives data transmitted from the information terminal 100 or the medical information management system 200 and transfers the data to a proper block.

Implementations

Figure 4:
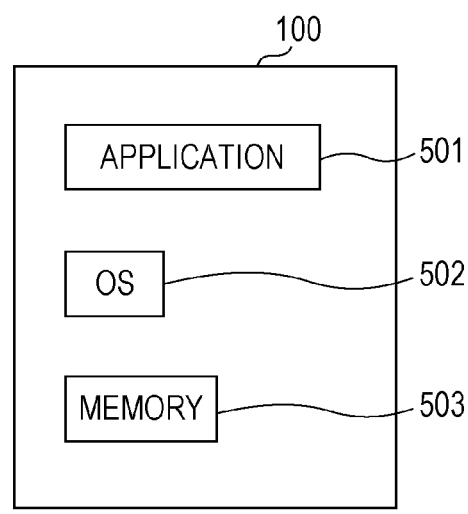
FIG. 4 is a diagram illustrating an example of a configuration in which an information terminal is implemented.

FIG. 4 is a diagram illustrating an example of an implementation of the information terminal 100. As illustrated in FIG. 4, the information terminal 100 includes an application 501, an operating system (OS) 502, a memory 503, and other hardware (not shown).

The application 501 is application software for enabling a personal computer or a tablet terminal to function as the information terminal 100, and is executed by a processor in the information terminal 100. The information terminal 100 may read out the application 501 from a computer-readable storage medium and install the application 501, or may download the application 501 via a network and installed it.

The application 501 includes a medical information management application and a similar case search application. The medical information management application is an application for enabling the information terminal 100 to cooperate with the medical information management system 200. The similar case search application is an application for enabling the information terminal 100 to cooperate with the case search system 300. The two applications transmit and receive data to and from each other such that service provided by the medical information management system 200 and service provided by the case search system 300 are integrated on the information terminal 100.

The OS 502 is basic software of the information terminal 100 and is executed by the processor of the information terminal 100. The memory 503 is realized using a storage apparatus such as a RAM, a ROM, or the like disposed in the information terminal 100, and stores data sets included in the application 501.

The processor of the information terminal 100 executes the application 501 thereby realizing functions of the input control unit 103, the display control unit 104, the ROI management unit 105, the name-of-disease management unit 108, the distribution type list management unit 109, and the communication control unit 110, shown in FIG. 2.

The present embodiment may be implemented on the information terminal 100 by using only the application 501, or using the application 501 and the OS 502. Alternatively, the present embodiment may be implemented using the application 501, the OS 502, and the memory 503 may be installed, or the application 501, the OS 502, the memory 503, and other hardware (not illustrated). By any implementation described above, it is possible to realize the information terminal 100 according to the present embodiment.

Flow of Interpretation Process and Display Screen

FIG. 5 is a diagram illustrating an example of a basic screen K1 that is to be displayed on the display 101a immediately after the similar case search application is started on the information terminal 100. In FIG. 5, the basic screen K1 includes four medical image viewers 610 to 640. Medical images are generally recorded in a digital imaging and communication in medicine (DICOM) format, and the medical image viewers 610 to 640 are viewers capable of handling the DICOM format. In the present embodiment, it is assumed by way of example that medical images are chest CT images including a large number of tomographic images (hereinafter also referred to as slice images) in the DICOM format. However, alternatively, medical images may be CT images of another part (such as a head, an abdomen, a feet, an arm, or the like).

The slice images of chest CT images displayed in the medical image viewers 610 to 640 are changed according to an operation of a mouse or a keyboard. The slice images of the chest CT images may be arranged, for example, in the order from a neck toward an abdomen.

For example, when a mouse pointer is positioned on the medical image viewer 610 and a rotation of a mouse wheel is detected by the input control unit 103, the display control unit 104 changes the slice image displayed in the medical image viewer 610 depending on the detected amount of rotation. More specifically, for example, if, in the medical image viewer 610, the mouse wheel is rotated by an amount corresponding to one click in a backward direction seen from the mouse, then the display control unit 104 changes the currently displayed slice image to a slice image at a next slice position. On the other hand, for example, in a case where in the medical image viewer 610, the mouse wheel is rotated by an amount corresponding to one click in the forwarded direction seen from the mouse. then the display control unit 104 changes the currently displayed slice image to a slice image at a previous slice position. Thus a user such as a doctor is capable of searching for a desired slice image while properly changing the slice image displayed in the medical image viewer 610 by rotating the mouse wheel in the forward or backward direction.

As for the medical images, magnetic resonance imaging (MRI) images may be employed instead of chest CT images. Although four medical image viewers are provided in the example shown in FIG. 5, the number of medical image viewers is not limited to four, but six, eight, or other numbers of medical image viewers may be employed. As the number of medical image viewers increases, the number of images subjected to the comparison increases, although the display area size per image decreases. Therefore, the number of medical image viewers may be set properly depending on the display size of the display 101a. In the present embodiment, the number of medical image viewers may be freely changed by a user or an administrator.

Before the similar case search application is started, slice images of chest CT images of a certain patient are displayed over the entire area of the display 101a. In this situation, if the similar case search application is started by a user such as an image interpreter or the like, the slice images displayed on the whole area of the display 101a are displayed in the medical image viewer 610.

Search query images displayed over the whole area of the display 101a are displayed as initial images in the medical image viewer 610 when the similar case search application is started by a user. Note that the display control unit 104 may displays images such that a region of interest in similar case search is superimposed on the search query image. Note that the search query image is an example of a target medical image, which is a medical image to be interpreted. The region of interest is specified by an area enclosed in a rectangle in a medical image displayed in the medical image viewer 610. In other words, the region of interest is a continuous area enclosed in a rectangle. Alternatively, the region of interest may be an area enclosed in a circle, a polygon, or another shape in a medical image as long as it is possible to distinguish between the region of interest and the other area.

In FIG. 5, no images are displayed in other medical image viewers 620 to 640. In a case where there are a plurality of examination images of a patient to be subjected to diagnosis, and a plurality of examination images are displayed on the display 101a before the similar case search application is started, the display control unit 104 may display these examination images in the medical image viewers 620 to 640.

FIG. 6 is a diagram illustrating an example of a basic screen K2 displayed on the display 101b immediately after the similar case search application is started on the information terminal 100. The basic screen K2 shown in FIG. 6 includes a case display area 710, a name-of-disease list display area 730, and a distribution type list display area 750. The case display area 710 is an area in which thumbnail images (axial images) of a similar case similar to a search query image are displayed in the order of similarity level. Herein, the thumbnail image of the similar case is an example of a similar medical image.

Figure 7:
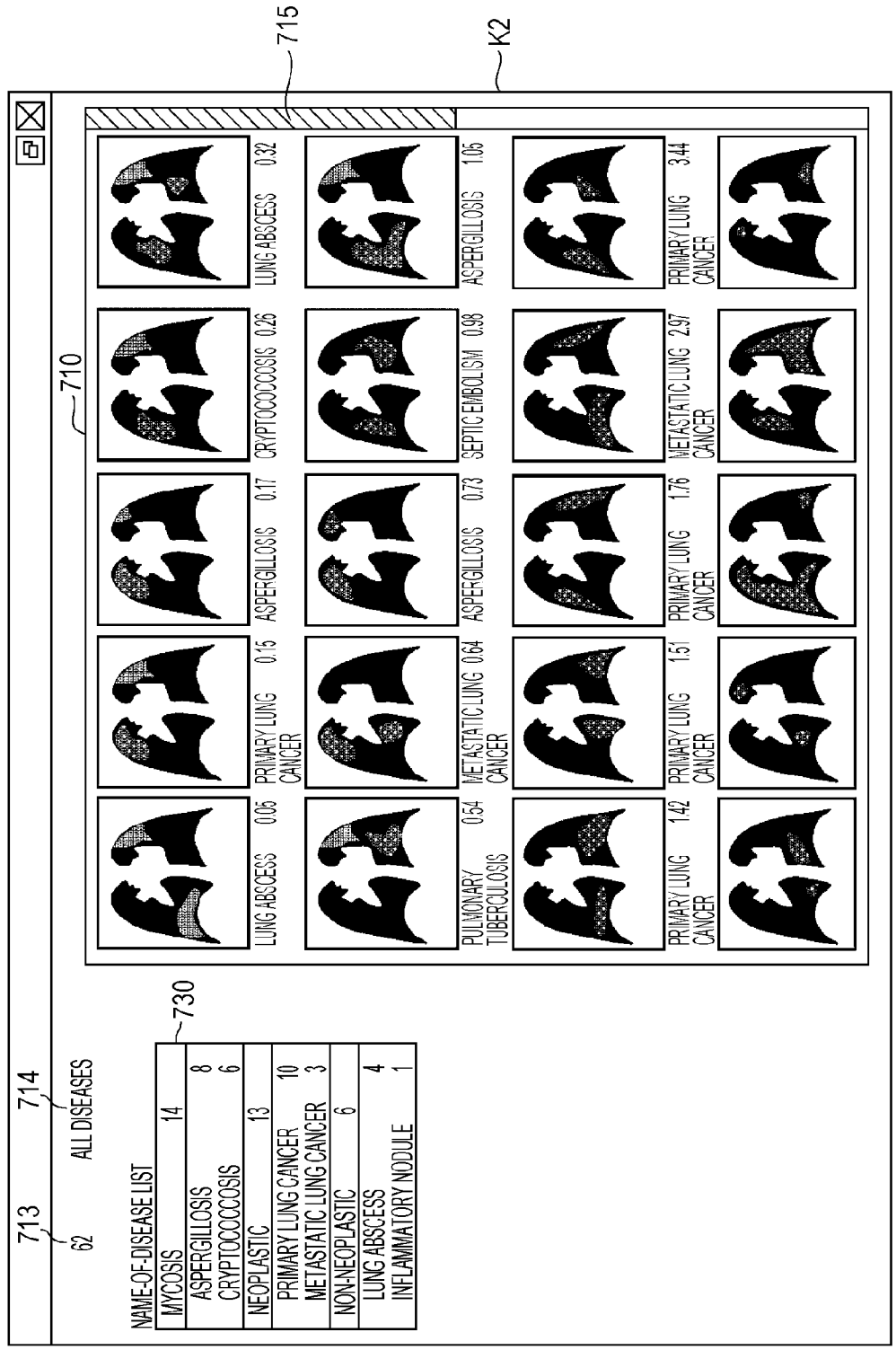
FIG. 7 is a diagram illustrating an example of a basic screen that is to be displayed on a display immediately after a similar case search application is started on an information terminal in a case where two or more regions of interest are set in a search query image or in a case where no region of interest is set.

FIG. 7 is a diagram illustrating an example of a basic screen K2 displayed on the display 101b immediately after the similar case search application is started on the information terminal 100 for a case where two regions of interest are set on the search query image or no region of interest is set. The basic screen K2 shown in FIG. 7 includes a case display area 710 and a name-of-disease list display area 730. The case display area 710 is an area in which thumbnail images (coronal images) of a similar case similar to a search query image are displayed in the order of similarity level. Herein, the thumbnail image of the similar case is an example of a similar medical image.

In the basic screen K2 shown in FIG. 6, axial images are displayed as the thumbnail images of the similar case. In the basic screen K2 shown in FIG. 7, coronal images are displayed as the thumbnail images of the similar case. Note that axial images are images of cross sections perpendicular to a body axis. In other words, the axial images are images of cross sections perpendicular to a longitudinal direction of a user. In the present description, the term "perpendicular" is used to describe a direction perpendicular to the body axis (longitudinal direction) of a user with an error that may occur when the images are captured. The coronal images are cross-section images taken along a plane that divides a body into front and back parts. Note that in the present description, the coronal images are not limited to cross-section images taken along a plane extending to a direction from left to right of a body such that each cross-section image is divided into front and back parts, but the images may be divided in a diagonal direction (for example, within range of an angle of about 45°) by a plane. In other words, the coronal image is an image of a cross section taken in a direction within a range of angle from 0° to 45° with respect to a plane parallel to the axis in the longitudinal direction of a user. Herein the angle in the range of angle from 0° to 45° with respect to the plane parallel to the axis in the longitudinal direction of a user may include an error that may occur when the images are captured. That is, the angle of the cross section of the coronal image may fall within a range from 0°–an error occurring when the image is captured to 45°+an error occurring when the image is captured.

In the following description, it is assumed by way of example that axial image displays are displayed. However, also in the case where coronal images are displayed, thumbnail images are generated and a name-of-disease list is displayed in a similar manner as described below.

Many similar cases are displayed in the case display area 710, and thus, if a process of changing resolution or pixel values is performed on a real-time basis, it will take a long time to perform the process. To avoid such a situation, thumbnail images are produced in advance from original slice images and stored in the case search system 300.

A further description is given below as to the process of converting resolution or pixel values. The original slice images have a resolution of 512×512 pixels, while the thumbnail images have a lower resolution, and thus it is necessary to perform a resolution conversion. Thus, thumbnail images are generated via a resolution reduction process and a gray-level conversion process performed on original slice images.

The gray-level conversion process is performed, for example, as follows. Each pixel value (CT value) of a slice slice image acquired by CT is in a range from −1000 to +1000 HU (Hounsfield Unit) and thus it is impossible to directly display it on a 8-bit gray-level display. Even if it is possible to display such an image with 2000 gray level, it is difficult for human eyes to visually distinguish among a lung emphysema area (CT value: −1000 HU), a normal tissue in a lung field (CT value: bout −900 HU) a frosted glass area (CT value: −800 HU), a soft tissue (CT value: −100 to −50 HU), water (CT value: 0 HU), and a bone (CT value: 1000 HU).

Therefore, in general, for slice images, a window level and a window width are defined, and pixel values are converted into 8-bit pixel values and displayed on the display. Note that the window level indicates a CT value at a center of the window, while the window width indicates the width of the window around the center of the window.

For example, in a case where a DICOM image is reconstructed in lung window setting, the window level is set in a range from −550 to −800, and the window width is set in a range from 1000 to 1600. A thumbnail image thereof is generated from the original slice image by performing the process described above such that the pixel values are converted into 8-bit values.

Note that thumbnail images displayed in the case display area 710 are thumbnail images of similar cases whose distance to a feature vector of a target case to be diagnosed is equal to or smaller than a threshold value. The distance used here may be a Euclidean distance. Note that the distance may be defined in other ways. For example, a city block distance or the like may be employed. The smaller the distance between two images the comparison, the higher the similarity. Note that the feature vector employed here is generated not from a thumbnail image but from an original slice image.

Figure 8:
FIG. 8 is a diagram showing one of similar case display areas displayed in a case display area.

FIG. 8 is a diagram showing a display area 701 of a similar case taken from those displayed in the case display area 710. A thumbnail image is displayed in the similar case display area 701, and a diagnosed disease name display area 711 and a distance display area 712 are disposed below the thumbnail image. In the diagnosed disease name display area 711, a definitively diagnosed disease name of a similar case of interest is displayed. Note that the definitively diagnosed disease name refers to a name of disease determined via diagnosis on a similar case of interest. In the distance display area 712, the distance between a feature vector of a slice image of a similar case of interest and a feature vector of a search query image is displayed. In the example shown in FIG. 8, "nontuberculous mycobacteriosis" is displayed in the diagnosed disease name display area 711, and thus this thumbnail image is a thumbnail image of a similar case that has been definitively diagnosed as "nontuberculous mycobacteriosis". Furthermore, "0.05" is displayed in the distance display area 712 to indicate that the distance between the slice image of this similar case and the search query image is "0.05".

As shown in FIG. 8, a thumbnail image displayed in a similar case display area 701 include a corresponding region of interest CROI. The corresponding region of interest CROI is an area corresponding to a region of interest set in a search query image (a medical image to be interpreted), that is, the corresponding region of interest CROI is similar to the region of interest. Hereinafter, the corresponding region of interest will also be referred to simply as "region of interest".

Referring again to FIG. 6, a number-of-hits display area 713 is disposed, for example, on the upper left of the basic screen K2. The value displayed in the number-of-hits display area 713 indicates the number of similar cases similar to the target case to be diagnosed, obtained as a result of the search process from the case search system 300.

In a case where there are a huge number of similar cases, it is impossible to display all similar cases at a time in the case display area 710. To handle this situation, a vertical scrollbar 715 is disposed, for example, on the right-side edge of the case display area 710. The display control unit 104 scrolls the thumbnail image displayed in the case display area 710 in the vertical direction depending on the amount of movement of the scrollbar 715. This makes it possible for a user to display previously-hidden similar cases in the case display area 710 to watch them.

Alternatively, the scrollbar 715 may be a horizontal scrollbar. In this case, the display control unit 104 scrolls the thumbnail image displayed in the case display area 710 in the horizontal direction depending on the amount of movement of the scrollbar 715. Alternatively, the display control unit 104 may scroll the thumbnail images displayed in the case display area 710 such that when the mouse pointer points to a particular location in the case display area 710, if an arrow key on the keyboard is pressed, then the display control unit 104 scrolls the thumbnail images in a direction indicated by the pressed arrow key as long as the arrow key is pressed.

In the example described above, the information terminal 100 acquires thumbnail images whose distance from the search query image is equal to or smaller than the predetermined threshold value from the case search system 300. However, this is merely an example. For example, the information terminal 100 may acquire a fixed number of thumbnail images having highest similarity levels from the case search system 300. Alternatively, the information terminal 100 may acquire thumbnail images from the case search system 300 such that the acquired thumbnail images include a fixed number of thumbnail image of a particular definitively diagnosed disease name.

The thumbnail images in the case display area 710 may be displayed, for example, such that a thumbnail image with the smallest distance from the search query image is displayed on the left-hand end in the top row, and other thumbnail images are displayed in this row from left to right in the ascending order of distance. When thumbnail images displayed in a certain row reach the right-side end, remaining thumbnail images are displayed in a similar manner starting at the left-hand end in a next row in the ascending order of distance. That is, in the case display area 710, thumbnail images are displayed in a zig-zag fashion in the ascending order of distance from the left to the right and from the top to the bottom.

In the present embodiment, the manner of displaying thumbnail images is not limited to that described above. For example, thumbnail images may be displayed such that a thumbnail image with the smallest distance from the search query image is displayed on the top in the leftmost column, and other thumbnail images are displayed in this column in a downward direction in the ascending order of distance. When thumbnail images displayed in a certain column reach the bottom, remaining thumbnail images are displayed in a similar manner starting at the top in a next column in the ascending order of distance. A user may be allowed to switch among a plurality of manners of displaying thumbnail images.

In the example described above, the distance is used to express the similarity level. However, other measures such as a cosine similarity level may be used to express the similarity between images as long as it is capable of expressing the similarity between images. In a case where the cosine similarity level is employed, as the value approaches 1, the similarity between two images under comparison increases.

The similar cases displayed in the case display area 710 may be narrowed according to the name of disease displayed in the name-of-disease list display area 730 or the lesion distribution displayed in the distribution type list display area 750, as will be described in further detail below. A current narrowing condition for similar cases is displayed in a display-condition display area 714. In the example shown in FIG. 6, displayed similar cases are in a state immediately after similar case searching is performed, and no further narrowing is performed. Thus "all diseases" is displayed in the display-condition display area 714.

Name-of-Disease List

Referring again to FIG. 6, the name-of-disease list display area 730 with a title of "name-of-disease list" is disposed on the top in a left-hand area of the basic screen K2. In the name-of-disease list display area 730, definitively diagnosed disease names are displayed for all similar cases acquired as a result of searching for similar cases. After the target case to be diagnosed is diagnosed and given a definitively diagnosed disease name, it is accumulated as one of similar cases in the case search system 300. That is, each similar case has a definitively diagnosed disease name determined via diagnosis and given before being accumulated in the case search system 300.

FIG. 9 is a diagram illustrating, in an enlarged manner, the name-of-disease list display area 730. In the name-of-disease list display area 730 shown in FIG. 9, each definitively diagnosed disease name has a broadly-classified disease name (731, 734, 737, 741, 744) and a finely-classified disease name (732, 733, 735, 736, 738, 739, 740, 742, 743, 745). In the example shown in FIG. 6, broadly-classified disease names displayed include mycosis 731, neoplastic 734, nonneoplastic 737, mycobacteriosis 741, and others 744.

In the example shown in FIG. 9, mycosis 731 is further classified into finely-classified disease names, that is, aspergillosis 732, and cryptococcosis 733. Similarly, neoplastic 734 is further classified into finely-classified disease names, that is, primary lung cancer 735, and metastatic lung cancer 736. Furthermore, nonneoplastic disease 737 is further classified into finely-classified disease names, that is, lung abscess 738, sarcoidosis 739, and septic embolism 740. Similarly, mycobacteriosis 741 is further classified into finely-classified disease names, that is, nontuberculous mycobacteriosis 742, and pulmonary tuberculosis 743. Furthermore, others 744 are further classified into a finely-classified disease name, that is, bronchiectasis 745.

Figure 10:
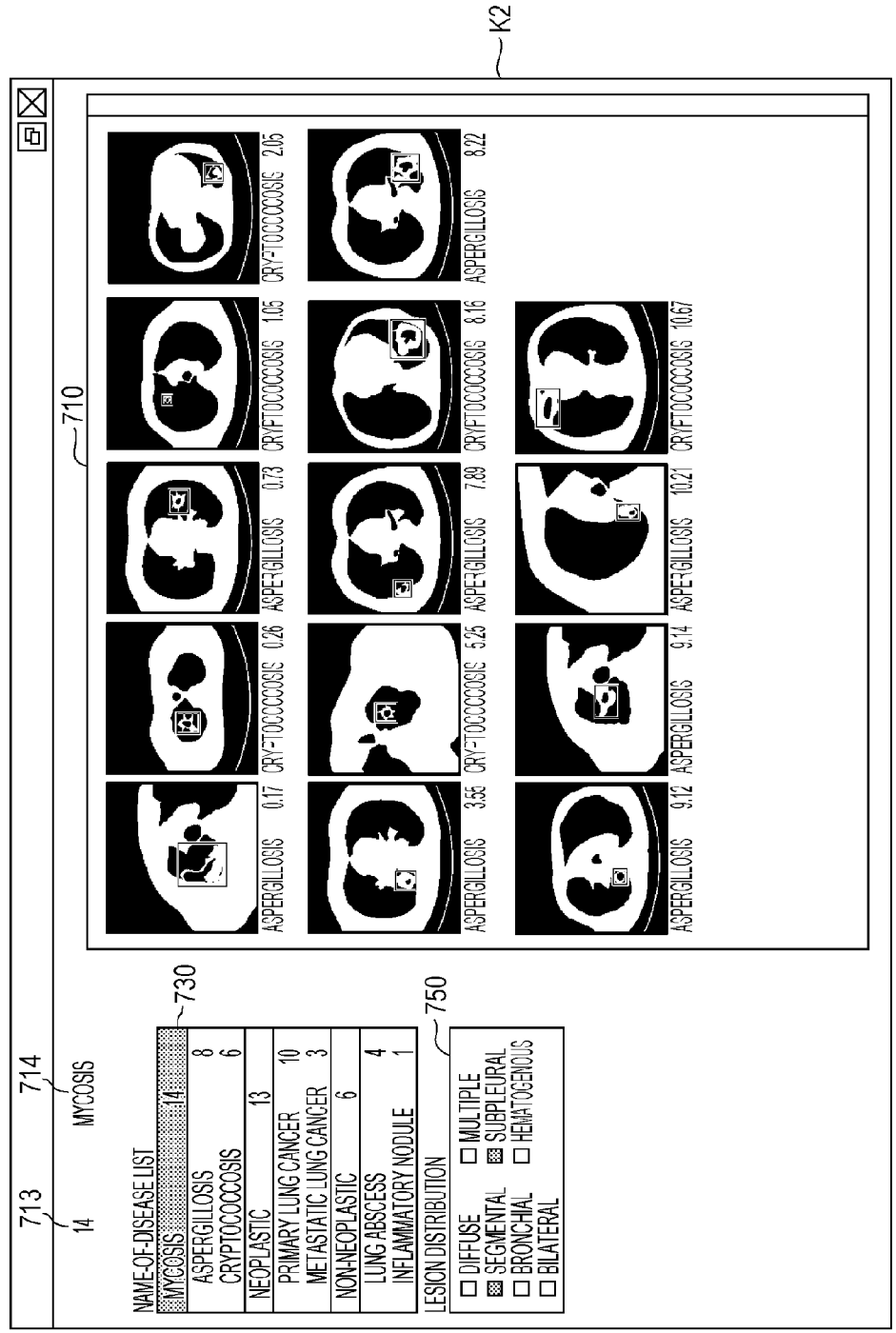
FIG. 10 is a diagram illustrating a basic screen displayed when similar cases are narrowed by "mycosis"

The number of cases is displayed to the right of each broadly-classified disease name and also each finely-classified disease name. A user is allowed to narrow similar cases displayed in the case display area 710 by selecting a row corresponding to a particular broadly-classified disease name or finely-classified disease name in the name-of-disease list display area 730. In a state immediately after searching for similar cases is performed, there are 62 similar cases of a variety of diseases that can be displayed as shown in FIG. 6. In FIG. 9, in a case where a row corresponding to mycosis 731 is clicked with a mouse, the display control unit 104 displays only similar cases of mycosis in the case display area 710 as shown in FIG. 10. On the other hand, in FIG. 9, in a case where a row corresponding to metastatic lung cancer 736 is clicked with the mouse, the display control unit 104 displays only similar cases of metastatic lung cancer in the case display area 710 as shown in FIG. 11.

In this situation, the display control unit 104 displays a name of disease used to narrow the search result in the display-condition display area 714 in order to indicate a narrowing-down condition used to obtain the similar cases currently displayed in the case display area 710.

FIG. 10 is a diagram illustrating the basic screen K2 displayed when the similar cases have been narrowed according to "mycosis". FIG. 11 is a diagram illustrating the basic screen K2 displayed when the similar cases have been narrowed according to "metastatic lung cancer".

In the example shown in FIG. 10, the narrowing is performed according to "mycosis", and thus "mycosis" is displayed in the display-condition display area 714. In the example shown in FIG. 11, the narrowing is performed according to "metastatic lung cancer", and thus "metastatic lung cancer" is displayed in the display-condition display area 714.

In such a situation, the display control unit 104 displays the number of similar cases in the number-of-hits display area 713 in order to indicate the number of similar cases currently displayed in the case display area 710. In the example shown in FIG. 10, 14 similar cases of "mycosis" are obtained as a result of searching, and thus "14" is displayed in the number-of-hits display area 713. In the example shown in FIG. 11, 3 similar cases of "metastatic lung cancer" are obtained as a result of searching, and thus "3" is displayed in the number-of-hits display area 713.

This function makes it possible to display similar cases such that only similar cases associated with a name of disease assumed by a doctor in image diagnosis are displayed in the case display area 710 thereby allowing the doctor to easily confirm whether the target case to be diagnosed are consistent with the assumed name of disease.

In FIG. 10, M (M=14 in the example shown in FIG. 10) thumbnail images of the similar cases are displayed in the case display area 710 in which thumbnail images are allowed to be displayed up to ND thumbnail images (ND=20 in the present example).

Lesion Distribution

In FIG. 6, in a middle part of the left-hand area of the basic screen K2, the distribution type list display area 750 with a title of "lesion distribution" is disposed. In the distribution type list display area 750, lesion distribution types of all similar cases acquired as a result of searching similar cases from the case search system 300 are displayed.

FIG. 12 is a diagram illustrating, in an enlarged manner, the distribution type list display area 750. In the example shown in FIG. 12, 7 names of lesion distribution types are displayed, and a check box is disposed to the left of the name of each lesion distribution type. In the example shown in FIG. 12, the lesion distribution types displayed include "diffuse" 751 (diffuse type), "segmental" 752 (segmental type), "bronchial" 753 (bronchial type), "bilateral" 754 (bilateral type), "multiple" 755 (multiple type), "subpleural" 756 (subpleural type), and "hematogenous" 757 (hematogenous type).

These lesion distribution types are defined in advance, and a distribution type flag value (set to 1 or 0) is assigned in advance to each similar case to indicate which one of lesion distribution types ("diffuse" 751 to "hematogenous" 757) the similar case has. Depending on the similar case, all distribution type flag values are set to 0, or a plurality of distribution type flag values are set to 1.

In the case search system 300 according to the present embodiment, searching is performed to retrieve similar cases having regions of interest similar to a region of interest set by a user in a slice image of a target case to be diagnosed. There is a possibility that there is a lesion in another slice image in addition to the slice image in which the region of interest is set by the user. There is also a possibility that after the searching is performed to retrieve similar cases having regions of interest similar to a region of interest set in the slice image, the user may want to compare another different slice image with the retrieved similar cases. In this case, the user may perform a slice forward operation on the medical image viewer 610 such that another slice image is displayed, and may compare it with the retrieved similar cases. In this case, if only similar cases associated with a lesion of interest selected from all retrieved similar cases are displayed in the case display area 710, then it is possible to easily perform an operation of extracting a slice image including a particular lesion of interest from the slice images other than the slice image in which the region of interest is set. In view of the above, in the present embodiment, a function is provided to make it possible to narrow the retrieved similar cases in terms of a particular lesion distribution type of interest thereby making it possible to perform the operation more easily.

In the present example, types of lesion distributions within a lung field area include "diffuse" 751 to "hematogenous" 757 shown in FIG. 12. Furthermore, as shown in FIG. 12, the display control unit 104 displays check boxes and lesion distribution types such that lesion distributions allowed to be narrowed are displayed in an active state while lesion distributions that are not allowed to be narrowed are displayed in an inactive state. More specifically, in the present example, the active state is represented by employing higher brightness than that of the inactive state.

In the example shown in FIG. 12, the "diffuse" distribution type 751, the "bronchial" distribution type 753, the "bilateral" distribution type 754, the "multiple" distribution type 755, the "subpleural" distribution type 756, and the "hematogenous" distribution type 757 are displayed in the active state, while the "segmental" distribution type 752 is displayed in the inactive state. This situation is a result of the setting performed such that, of all similar cases acquired as a result of similar case search, the distribution type flag value is set to 1 ("true") in terms of "diffuse" 751, "bronchial" 753, to "hematogenous" 757 for at least one of the similar cases, while the distribution type flag value in terms of the "segmental" 752 is set to 0 ("false") for all retrieved similar cases.

If the input control unit 103 detects that one or more check boxes of those in the active state are checked, the display control unit 104 displays only similar cases corresponding to checked lesion conditions in the case display area 710.

As for the "segmental" distribution type 752, the distribution type flag value is set to 0 ("false") for all similar cases obtained as a result of the search. Therefore, if the "segmental" distribution type 752 is allowed to be checked in this situation, then in a case where a check box of this lesion distribution type is checked, no similar case is displayed in the case display area 710, which means that checking the check box is useless. In the present embodiment, to avoid such a situation, in a case where the distribution type flag value is set to 0 ("false") for all similar cases of a particular lesion distribution type obtained as a result of the search, this particular lesion distribution type is displayed in the inactive state.

Figure 14:
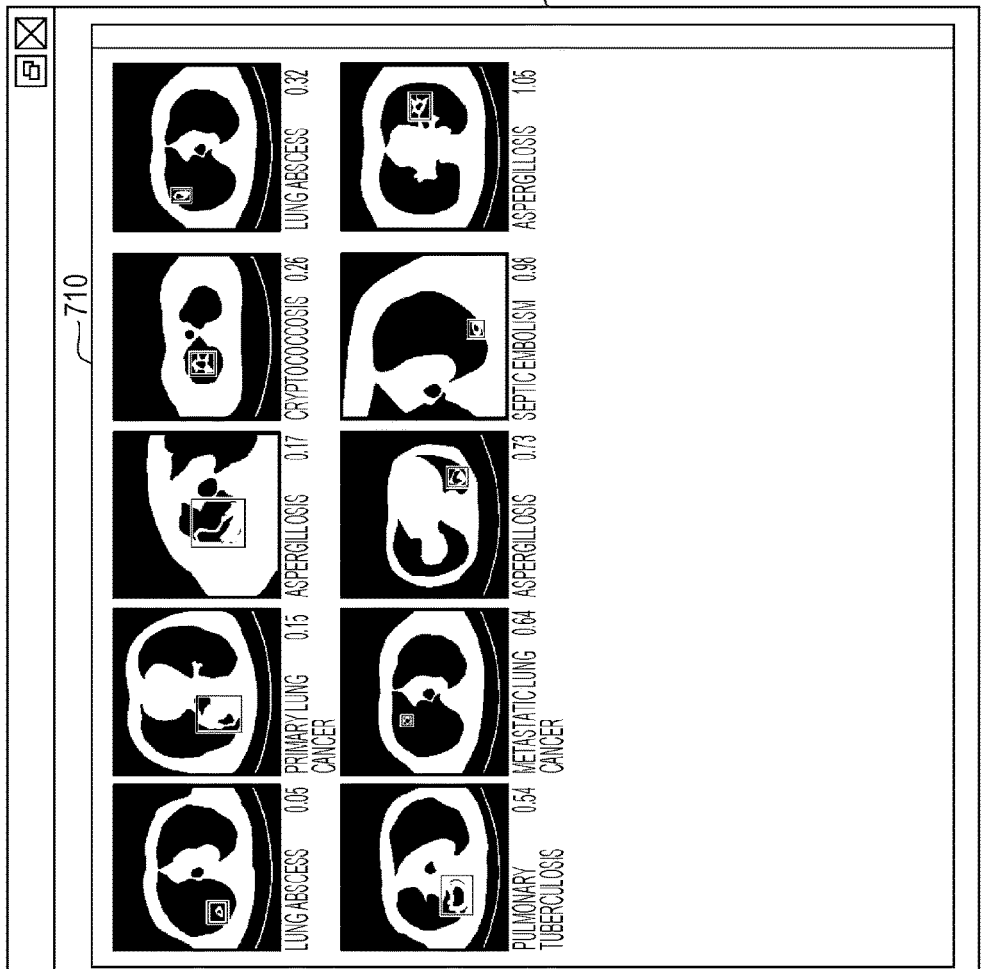
FIG. 14 is a diagram illustrating a basic screen displayed when narrowing is performed by a bilateral lesion distribution.

FIG. 13 is a diagram illustrating the distribution type list display area 750 in a state in which the check box of "bilateral" 754 is checked. FIG. 14 is a diagram illustrating the basic screen K2 displayed when narrowing is performed according to the "bilateral" lesion distribution type. In a case where the check box of "bilateral" 754 is checked as shown in FIG. 13, the display control unit 104 displays only similar cases having a bilateral lesion distribution in the case display area 710 as shown in FIG. 14. In this example, there are 10 similar cases having the bilateral lesion distribution. Therefore, the display control unit 104 displays "10" in the number-of-hits display area 713. The display control unit 104 displays, in the display-condition display area 714, the name of disease to be displayed and "bilateral" which is the name of the lesion distribution type. In the example shown in FIG. 14, narrowing according to one of disease names listed in the name-of-disease list display area 730 is not performed, and thus "all diseases" is displayed in the display-condition display area 714.

Patient Information 1000

FIG. 15 is a diagram illustrating a data structure of patient information 1000. The patient information 1000 is accumulated for each patient in the patient information accumulation unit 201 by the patient information management unit 202 in the medical information management system 200. In the patient information 1000, personal information such as a gender, an age, and the like of a patient, clinical information such as an anamnesis, and medical examination information such as a blood test are registered. As shown in FIG. 15, the patient information 1000 includes a patient ID 1100, a name 1200, an age 1300, a gender 1400, an anamnesis 1500, a family history 1600, a chief complaint 1700, medical examination information 1800, and a definitive diagnosis 1900.

The patient ID 1100 is an identifier uniquely assigned to a patient. The name, the age, the gender, the anamnesis, the family history, and the chief complaint of the patient of the patient ID 1100 are respectively described in the name 1200, the age 1300, the gender 1400, the anamnesis 1500, the family history 1600, and the chief complaint 1700. As shown in FIG. 16, the medical examination information 1800 represents information on one or more examinations the patient has had in the past.

FIG. 16 is a diagram illustrating a data structure of the medical examination information 1800 registered in the patient information 1000 shown in FIG. 15. The medical examination information 1800 is information associated with examinations taken by the patient, and one set of medical examination information 1800 is produced individually for each examination. The medical examination information 1800 includes an examination ID 1810, an examination date/time 1820, an examination item 1830, and an examination result 1840. The examination ID 1810 is an identifier uniquely assigned to each examination. The examination date/time 1820 represents date/time of the examination. The examination item 1830 represents an examination item. Examples of examination items include a blood test, a respiratory function test, an endoscopy test, a simple X-ray test, and a CT scan test.

For example, in the case of the blood test, the examination result 1840 represents index values in terms of the number of leukocytes, LDH, GPT, and the like. The examination result 1840 may also include a diagnosis made by a doctor based on the index values. In the case of an image examination such as simple X-ray test, CT scan test, or the like, the examination result 1840 may include pointer information pointing to a captured image, pointer information pointing to a report on an image diagnosis result, and the like. Note that an image captured in an examination is accumulated in the DICOM format in the medical image data accumulation unit 203 in the medical information management system 200.

In the case where the examination item 1830 is an image examination using simple X-ray, CT, MRI, PET, or the like, medical image data obtained in the image examination is accumulated in the medical image database 2000 stored in the medical image data accumulation unit 203 of the medical information management system 200.

Figure 17:
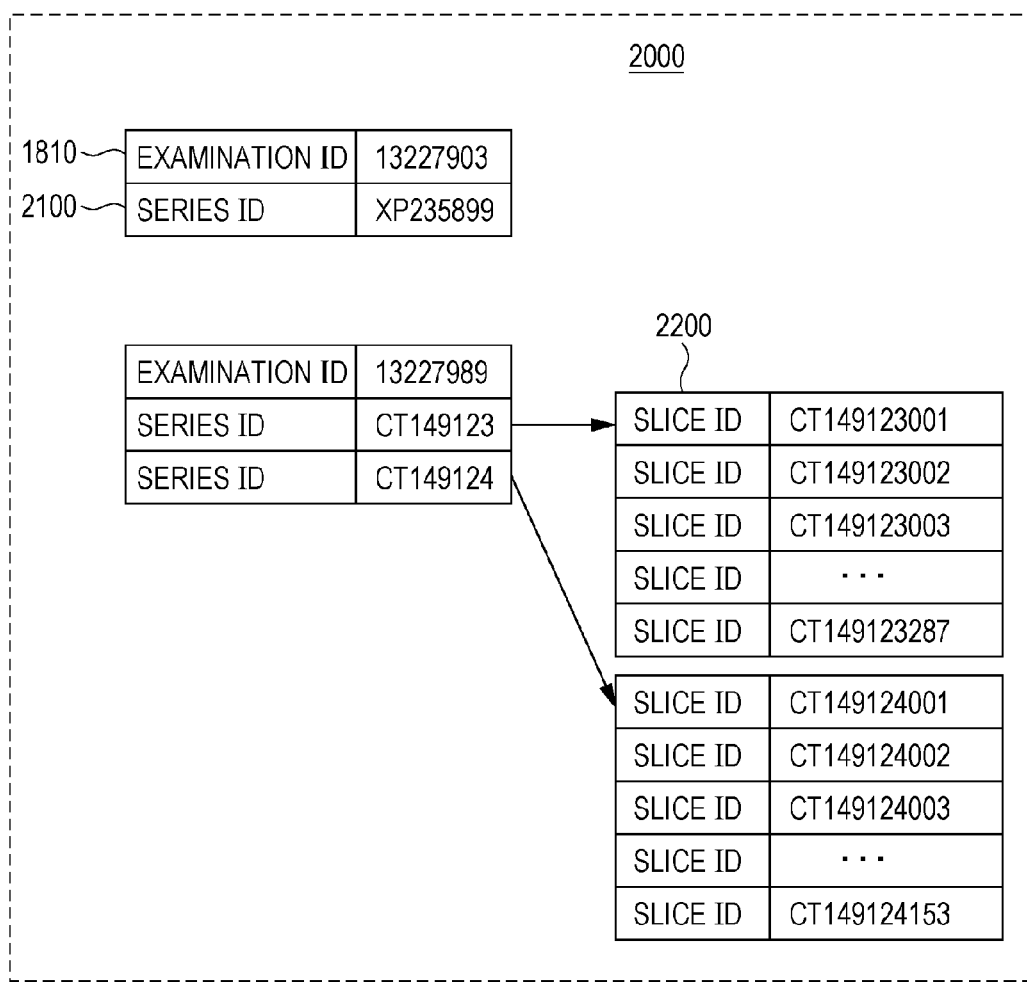
FIG. 17 is a diagram illustrating a data structure of a medical image database.

FIG. 17 is a diagram illustrating a data structure of the medical image database 2000. The medical image database 2000 includes an examination ID 1810 and a series ID 2100. There is a possibility that a plurality of types of image examination (for example, simple CT and contrast CT, or the like) are performed in one examination, and thus one examination ID 1810 may be related to a plurality of series IDs 2100. That is, there may be as many series as the number of image examinations.

One series is obtained for each captured-image reconstruction condition, in addition to, for each image examination. For example, in a case where a captured image is reconstructed according to a lung window setting and a mediastinal window, one series is obtained for each of these conditions. Note that in the image reconstructed according to the lung window setting, blood vessels, a bronchus, alveoli, and the like in the lung are displayed in a highlighted manner. In a case where the image is reconstructed according to the mediastinal window, mediastina such as blood vessels, lymph nodes, and the like are displayed in a highlighted manner. The lung window setting and the mediastinal window can be obtained by reconstructing images obtained in one run of imaging operation. Therefore, in a case where one run of imaging operation is performed for each of simple CT and contrast CT, and images are reconstructed in terms of lung window setting and mediastinal window for each run of CT and contrast CT imaging operations, two lung window setting series and two mediastinal window series are obtained.

In the case of the image examination using CT or MRI, a plurality of slice images are obtained as a result of one run of imaging operation, and thus one series ID 2100 are related to a plurality of slice IDs 2200. In FIG. 17, an examination ID "13227989" is related to two series IDs "CT149123", and "CT149124", which indicates that two series of CT images have been obtained as a result of this examination. It is also seen from FIG. 17 that the series IDs "CT149123" and "CT149124" are respectively related to a plurality of sets of slice IDs 2200.

In a case where the examination item 1830 is an image examination using simple X-ray, CT, MRI, PET or the like, the diagnosis report 3000 such as that shown in FIG. 18 is accumulated in the diagnosis report management unit 205 in the medical information management system 200. In the diagnosis report 3000, diagnosis results made by doctors on respective examinations are registered.

FIG. 18 is a diagram illustrating a data structure of the diagnosis report 3000. The diagnosis report 3000 includes an examination ID 1810, an observation 3100, and a diagnosis 3200. The examination ID 1810 is the same as the examination ID 1810 shown in FIG. 16, which relates the diagnosis report 3000 to the medical examination information 1800. In the observation 3100, a description of an observation given, for the examination, by a doctor is registered. In the diagnosis 3200, a description of a diagnosis given, for the examination, by a doctor is registered.

FIG. 19 is a diagram illustrating a data structure of similar case data 4000 of a localized lesion. The similar case data 4000 of a localized lesion is data used in searching a similar case similar to a target case to be diagnosed, and one piece of similar case data 4000 is generated for one similar case is generated. Note that the similar case data 4000 of a localized lesion is an example of additional information of similar case data. The similar case data 4000 is accumulated, for each similar case, in the similar case data accumulation unit 301 of the case search system 300. As shown in FIG. 19, the similar case data 4000 of localized lesion includes a similar case ID 4100, a slice ID 4200, region-of-interest information 4300, image feature data 4400, thumbnail image data 4500, lesion distribution information 4600, definitive diagnosis (broadly-classified disease name) 4700, and definitive diagnosis (finely-classified disease name) 4800.

The similar case ID 4100 is an identifier of the similar case data 4000 of localized lesion. In the case of a localized lesion, one piece of similar case data is generated for each region of interest set in a slice image of a similar case, and thus the similar case ID 4100 can be also said to an identifier of a region of interest. In the example shown in FIG. 19, the similar case ID 4100 includes a symbol string starting with "SIM" and following numerals.

The slice ID 4200 is an identifier of a slice image in which a region of interest is set, and is the same as the slice ID 2200 shown in FIG. 17. The region-of-interest information 4300 is information indicating a location of a region of interest set in a slice image. A region of interest is set in a slice image as described above with reference to FIG. 8. In the example shown in FIG. 8, a region of interest in the form of a rectangle is set. Therefore, the region-of-interest information 4300 includes four values indicating coordinates of an upper-left vertex and coordinates of a lower-right vertex of the region of interest. As a matter of course, the region of interest may be set in a form other than a rectangle. In this case, parameters that uniquely identify an area are employed as the region-of-interest information 4300. For example, in a case where a region of interest has a circular shape, coordinates of the center of the circle and a radius of the circle are employed as the region-of-interest information 4300.

The image feature data 4400 represents a feature value of a particular number of dimensions (N1 dimensions in the present example) extracted from the region of interest defined by the region-of-interest information 4300. The thumbnail image data 4500 is image data of a thumbnail image generated, so as to be displayed in the case display area 710, from a slice image in the DICOM format identified by the slice ID. The thumbnail image data 4500 includes, for example, pixel values of the thumbnail image such that the pixel values are arranged in the order of raster scanning starting from the upper-left vertex of the thumbnail image to the lower-right vertex of the thumbnail image. As described above, a DICOM image obtained as a result of a CT examination is an image including 512×512 pixels represented in 11-bit pixel values (−1000 to +1000). In the present embodiment, to achieve an increase in speed of displaying a thumbnail image, a thumbnail image with 8-bit pixel values is generated in advance by performing a resolution reduction process and a gray-level conversion process on an original DICOM image, and the resultant thumbnail image is registered in the similar case data 4000. The thumbnail image data 4500 of the similar case data 4000 of localized lesion is data of an axial image such as that shown in FIG. 6.

Note that the thumbnail image may be generated by the medical information management system 200 and transmitted to the case search system 300, or the case search system 300 may acquire a DICOM image from the medical information management system 200 and generate a thumbnail image from it.

The lesion distribution information 4600 is a distribution type flag value (1: "true", 0: "false") indicating whether a similar case of interest has a particular one of predefined lesion distribution types including "diffuse" 4610 to "hematogenous" 4670.

The definitive diagnosis (broadly-classified disease name) 4700 represents a broadly-classified disease name determined for a target similar case. The definitive diagnosis (broadly-classified name) 4700 is used in narrowing the similar cases according to a broadly-classified disease name.

The definitive diagnosis (finely-classified disease name) 4800 represents a finely-classified disease name determined for a similar case of interest. The definitive diagnosis (finely-classified disease name) 4800 is used in narrowing the similar cases according to the finely-classified disease name.

As for the definitive diagnosis (broadly-classified disease name) 4700, in advance, a broadly-classified disease name is assigned to definitive diagnosis (finely-classified disease name) 4800 and the definitive diagnosis (broadly-classified disease name) 4700 is stored, using the correspondence relation, in the similar case data 4000.

As for the definitive diagnosis (finely-classified disease name) 4800, in the medical image data accumulation unit 203, a series ID 2100 is identified from a slice ID 2200 shown in FIG. 17. From the identified series ID, an examination ID 1810 is identified in the patient information accumulation unit 201, and corresponding patient information 1000 (FIG. 15) is identified from the examination ID 1810. Furthermore, from the identified patient information 1000, a definitive diagnosis 1900 of a corresponding patient is identified.

FIG. 20 is a diagram illustrating a data structure of similar diffuse-lesion case data 5000. The similar diffuse-lesion case data 5000 is data that is to be referred to in searching for a similar case similar to a target case to be diagnosed, and one piece of similar case data 5000 is generated for one similar case. Note that the similar diffuse-lesion case data 5000 is an example of additional information of similar case data. The similar diffuse-lesion case data 5000 is accumulated, for each similar case, in the similar case data accumulation unit 301 of the case search system 300. As shown in FIG. 20, the similar diffuse-lesion case data 5000 includes a similar case ID 5100, a series ID 5200, image feature data 5300, thumbnail image data 5400, a definitive diagnosis (broadly-classified disease name) 5500, and a definitive diagnosis (finely-classified disease name) 5600.

The similar case ID 5100 is an identifier of the similar diffuse-lesion case data 5000. In the case of a diffuse lesion, one piece of similar case data is generated for each series, and thus the similar case ID 5100 can also be said to an identifier of a series. In the example shown in FIG. 20, the similar case ID 5100 includes a symbol string starting with "SIM" and a following numeral.

The series ID 5200 is an identifier of a series image in which a lesion area is set, and is the same as the series ID 2100 shown in FIG. 17.

The image feature data 5300 represents a feature value of a particular number of dimensions (N2 dimensions in the present example) of a whole internal organ extracted from an image of the series ID 5200. Note that the number of dimensions, N2, of the image feature data 5300 may or may not be equal to the number of dimensions, N1, of the image feature data 4400.

The thumbnail image data 5400 is image data of a thumbnail image generated, so as to be displayed in the case display area 710, from a slice image in the DICOM format identified by the series ID. For example, the thumbnail image data 5400 includes pixel values arranged in the order of raster scanning starting from the upper-left vertex of the thumbnail image to the lower-right vertex of the thumbnail image. In the present embodiment, like the thumbnail image data 4500, to achieve an increase in speed of displaying a thumbnail image, a thumbnail image with 8-bit pixel values is generated in advance by performing a resolution reduction process and a gray-level conversion process on an original DICOM image, and the resultant thumbnail image is registered in the similar case data 5000. The thumbnail image data 5400 of the similar diffuse-lesion case data 5000 is data of a coronal image such as that shown in FIG. 7.

Note that the thumbnail image may be generated, for example, by the medical information management system 200 and transmitted to the case search system 300, or the case search system 300 may acquire a DICOM image from the medical information management system 200 and generate a thumbnail image from it.

The definitive diagnosis (broadly-classified disease name) 5500 is similar to the definitive diagnosis (broadly-classified disease name) 4700 shown in FIG. 19, and the definitive diagnosis (finely-classified disease name) 5600 is similar to the definitive diagnosis (finely-classified disease name) 4800 shown in FIG. 19.

In the case of a diffuse lesion, the lesion extends over a whole internal organ, and thus the image feature data 5300 is given by a feature value of the whole internal organ. Therefore, in the case of a diffuse lesion, a region of interest is not set. Therefore, as shown in FIG. 20, unlike the similar case data 4000 of localized lesion, the similar diffuse-lesion case data 5000 does not include region-of-interest information.

Processing Flow

Next, a description is given below as to a processing flow, from a start of an image interpretation operation to a start of a similar case search, performed in cooperation by information terminal 100, the medical information management system 200, and the case search system 300.

Figure 22:
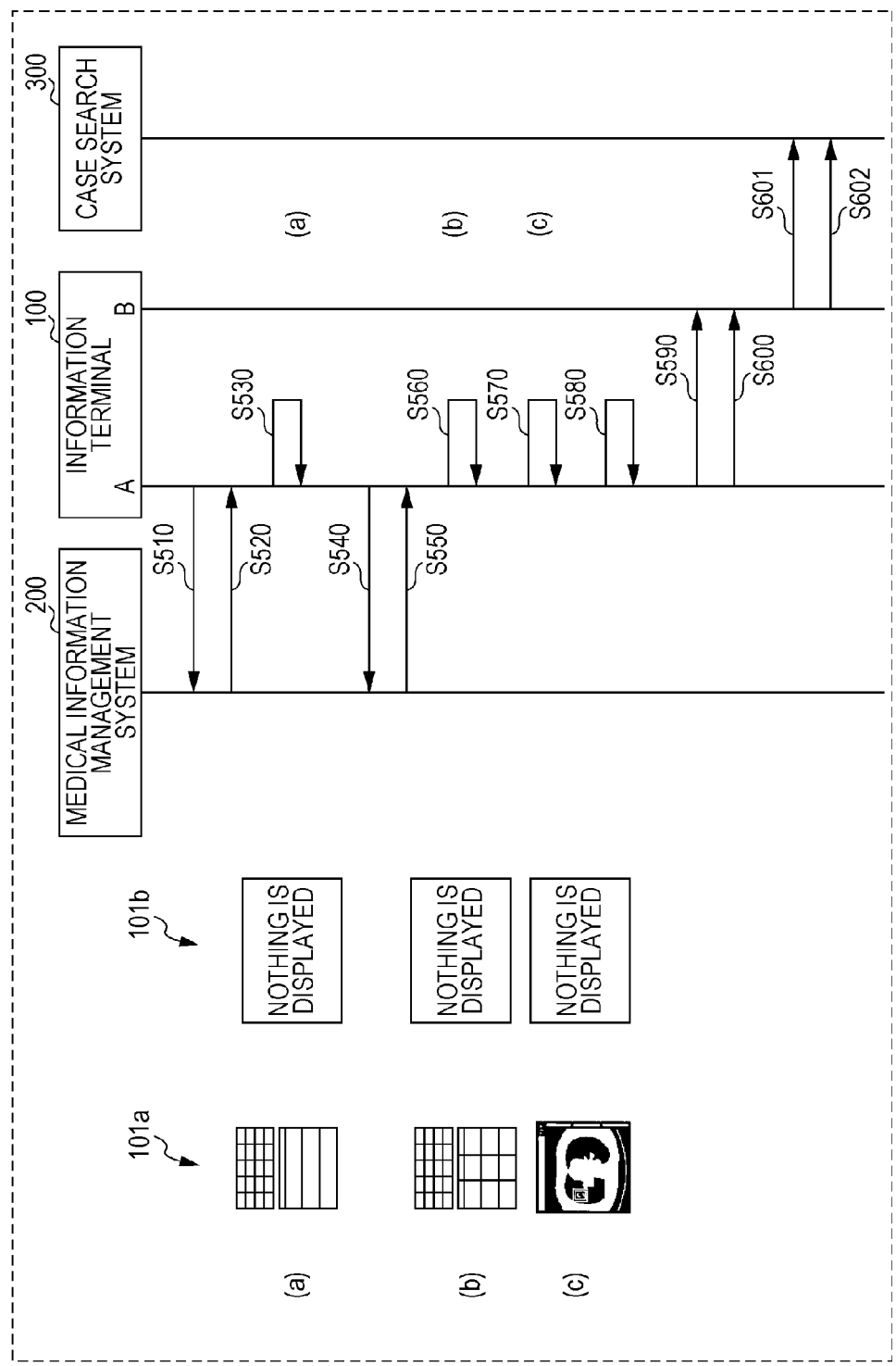
FIG. 22 is a sequence diagram illustrating a sequence, performed in a case where one region of interest is set by a user, from a step in which an information terminal acquires a target case to be diagnosed from a medical information management system and sends a similar case search request to a case search system to a step in which the case search system receives the similar case search request.

FIG. 22 is a sequence diagram illustrating a process performed, in a case where one region of interest is set by a user. The diagram shown here includes a sequence from a step in which the information terminal 100 acquires a target case to be diagnosed from the medical information management system 200 and sends a similar case search request to the case search system 300 to a step in which the case search system 300 receives the similar case search request. Note that, in FIG. 22, rectangles shown in two columns to the left of the sequence diagram respectively represent screens displayed on the displays 101*a* and 101*b* at particular steps in the process. In FIG. 22, "A" of the information terminal represents a medical information management application, while "B" represents a similar case search application. It is assumed here that the medical information management application has already been activated before the sequence is started.

First, the information terminal 100 accepts, via the operation unit 102, a request from a user (a doctor who interprets images) to display a list of examinations to be interpreted. The information terminal 100 transmits the request to display the list of examinations to the communication control unit 206 of the medical information management system 200 via the input control unit 103 and the communication control unit 110 (S510).

The patient information management unit 202 of the medical information management system 200 generates a list of examinations that have not yet been subjected to image interpretation after images were captured, that is, a list of examinations to be subjected to the image interpretation. The patient information management unit 202 then transmits the generated list of examinations to the communication control unit 110 of the information terminal 100 via the communication control unit 206 (S520). Note that the list of examinations includes the patient information 1000 and the medical examination information 1800 of a patient of interest.

The display control unit 104 of the information terminal 100 displays the list of examinations received via the communication control unit 110 on the display 101 (S530).

In this situation, the list of examinations is displayed on the display 101*a*, but nothing is displayed on the display 101*b*.

FIG. 23 is a diagram illustrating a screen of the list of examinations. The list of examinations includes an area 800 in which not-yet-interpreted examinations are displayed, and an area 810 in which information associated with series included in the examinations is displayed. The area 800 includes fields of "patient ID", "patient name", "examination date/time", "examination ID", and "examination item". In the fields of "patient ID" and the "patient name", the patient ID 1100 and the name 1200 registered in the patient information 1000 are respectively displayed. In the fields of "examination date/time", "examination ID", and "examination item", the examination date/time 1820, the examination ID 1810, and the examination item 1830, registered in the medical examination information 1800, are displayed. The area 810 is an area for displaying details of an examination selected in the area 800 by a user, and the area 810 includes fields of "series ID", "description", and "image". In the specific situation of the example, no examination (corresponding to a row) is selected in the area 800 by a user, and thus nothing is displayed in the area 810.

A user selects an examination to be interpreted from the examinations displayed in the area 800. If the selection is detected by the input control unit 103, then, as shown in FIG. 22, the communication control unit 110 sends, to the medical information management system 200, a request to display all series included in the examination IDs of the selected examination (S540).

When this display request is received by the communication control unit 206 of the medical information management system 200, the patient information management unit 202 refers to the medical image database 2000 shown in FIG. 17 and acquires all slice images of all series included in the examination ID specified by the display request. The patient information management unit 202 transmits the acquired slice images to the information terminal 100 via the communication control unit 206 (S550). In the example shown in FIG. 17, for example, if the examination of the examination ID "13227989" is selected by a user, all slice images included in the series of the series ID "CT149123" and the "CT149124" are transmitted in S550.

When the communication control unit 110 of the information terminal 100 acquires images of all series, the display control unit 104 displays a series list in the area 810 such that information associated with all series included in the specified examination ID is displayed in the list (S560).

In this case, the series list of series corresponding to the examination selected in the area 800 is displayed in the area 810 of the list of examinations displayed on the display 101a. However, nothing is displayed on the display 101b.

FIG. 24 is a diagram illustrating a screen of the list of examinations displayed after an examination is selected. In FIG. 24, a selected row in the area 800 is highlighted. More specifically, in the example shown in FIG. 24, an examination "Taro Pane" in the second row in the area 800 is selected. As a result, "series ID", "description", and "image" of the selected examination are displayed in the area 810. In the field of "series ID", series IDs related to the examination ID of the selected examination, in the medical image database 2000, are displayed. In the field of "image", a thumbnail image of one slice image typifying each of the displayed series IDs is displayed. As for one slice image typifying the series ID, an image at a particular slice position may be employed. As for the particular slice position, a starting slice position may be employed, or a middle slice position may be employed. In the field of "description", conditions in terms of an image-capturing condition, a reconstruction condition, and/or the like of the corresponding series are displayed. Although not shown in the figures, "description" is registered, for example, in the medical image database 2000 shown in FIG. 17, in relation to a corresponding series ID.

Figure 25:
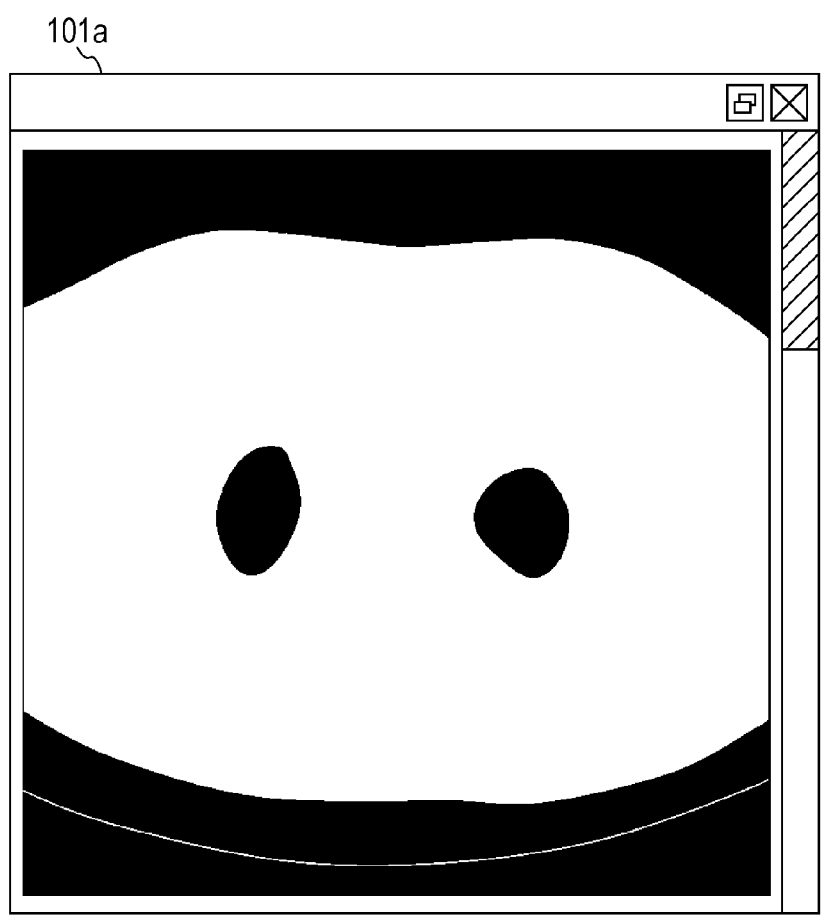
FIG. 25 is a diagram illustrating a slice image displayed on a display when a series is selected by a user.

If a series to be interpreted is selected in the area 810 by a user, and this selection is detected by the input control unit 103, then the display control unit 104 displays a slice image at a first position in the selected series on the display 101a as shown in FIG. 25 (S570).

FIG. 25 is a diagram illustrating the slice image displayed on the display 101a when the series is selected by the user. More specifically, in FIG. 25, the first slice image in images captured in a chest CT scan operation is displayed, wherein the first slice image is at a position of a shoulder slightly higher toward a head from a pulmonary apex region. In the displaying operation, the display control unit 104 displays the slice image on the display 101a such that it is allowed to sequentially change the slice image among the images of the selected series. Note that nothing is displayed on the display 101b. For example, when the mouse pointer is positioned on the display 101a by a user and the mouse wheel is rotated to issue a slice-change command, this operation is detected by the input control unit 103. In response, the display control unit 104 changes the slice image currently displayed on the display 101a to a slice image at another slice position depending on the amount of rotation of the mouse wheel. The user performs image diagnosis while performing the slice forward/backward operation. In a case where the user wants to watch a similar case in the image diagnosis, the user starts the similar case search application.

A shortcut key on the keyboard of the operation unit 102 may be predefined for use to start the similar case search application, and this shortcut key may be pressed to start the similar case search application. Alternatively, a menu of a medical image viewer may be displayed when the mouse is right-clicked, and the similar case search application may be started if a similar case search start button in the menu is selected. When a command to start the similar case search application is issued, controlling of the information terminal 100 is transferred to the ROI management unit 105, and the information terminal 100 goes to a state in which the information terminal 100 waits for a region of interest (ROI) to be input.

Figure 26:
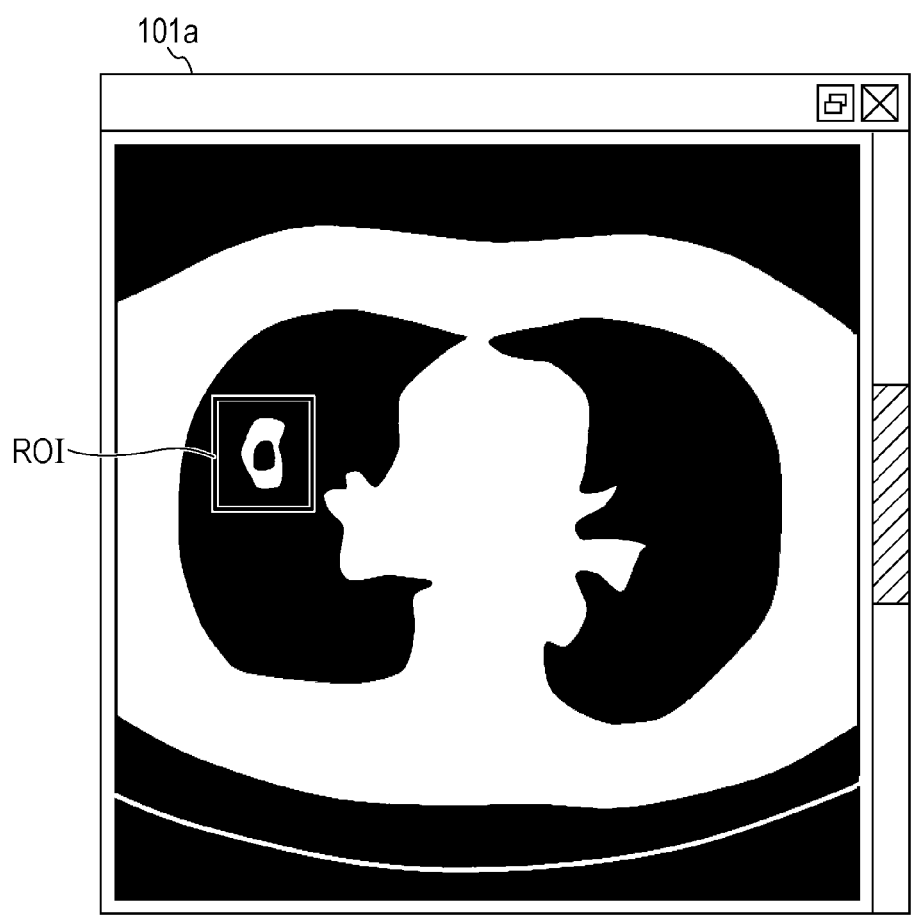
FIG. 26 is a diagram illustrating a slice image displayed on a display when a similar case search application is started by a user.

FIG. 26 is a diagram illustrating a slice image displayed on the display 101a when the similar case search application is started by a user. More specifically, FIG. 26 shows a slice image at a slice position to which the slice position has been changed from the first slice position shown in FIG. 25. The user sets, via the operation unit 102, one region of interest (ROI) on a lesion on the slice image displayed on the display 101a (S580). More specifically, for example, the user inputs coordinates of the upper-left vertex of the region of interest ROI on the slice image 3101 by left-clicking the mouse as illustrated in FIG. 26. The user drags the mouse in a right-down direction while keeping the mouse in the left-clicked state, and releases the left-clicking at the lower-right vertex of the region of interest ROI thereby inputting coordinates thereof.

When the operation of setting the region of interest is detected by the input control unit 103, the ROI management unit 105 receives coordinate data of the upper-left and lower-right vertices of the region of interest from the input control unit 103, and generates region-of-interest information including the received coordinate data. The ROI management unit 105 then transmits the generated region-of-interest information to the communication control unit 110 (S590). The ROI management unit 105 may generate information indicating the number of regions of interest (in the present example, the number of region of interests=1), and may put the information indicating the number of regions of interest in the region-of-interest information.

The number of regions of interest specified by the user is one, and thus the ROI management unit 105 also transmits a slice image of a target case to be diagnosed to the communication control unit 110 (S600).

When the communication control unit 110 receives the region-of-interest information transmitted from the ROI management unit 105, the communication control unit 110 transmits the received region-of-interest information to the communication control unit 304 of the case search system 300 (S601).

The communication control unit 110 also receives the slice image transmitted from the ROI management unit 105 and transmits the received slice image to the communication control unit 304 of the case search system 300 (S602).

In the example described above, the slice image is transmitted in S600 and S601. However, alternatively, the slice ID of the slice image may be transmitted without transmitting the slice image. In this case, when the case search system 300 receives the slice ID, the case search system 300 may acquire an image corresponding to the slice ID from the medical information management system 200.

In the present example, one region of interest is set by the user in S580. This suggests that the user wants to search for a localized lesion which is a lesion present only at one localized place as shown in FIG. 26.

Figure 44:
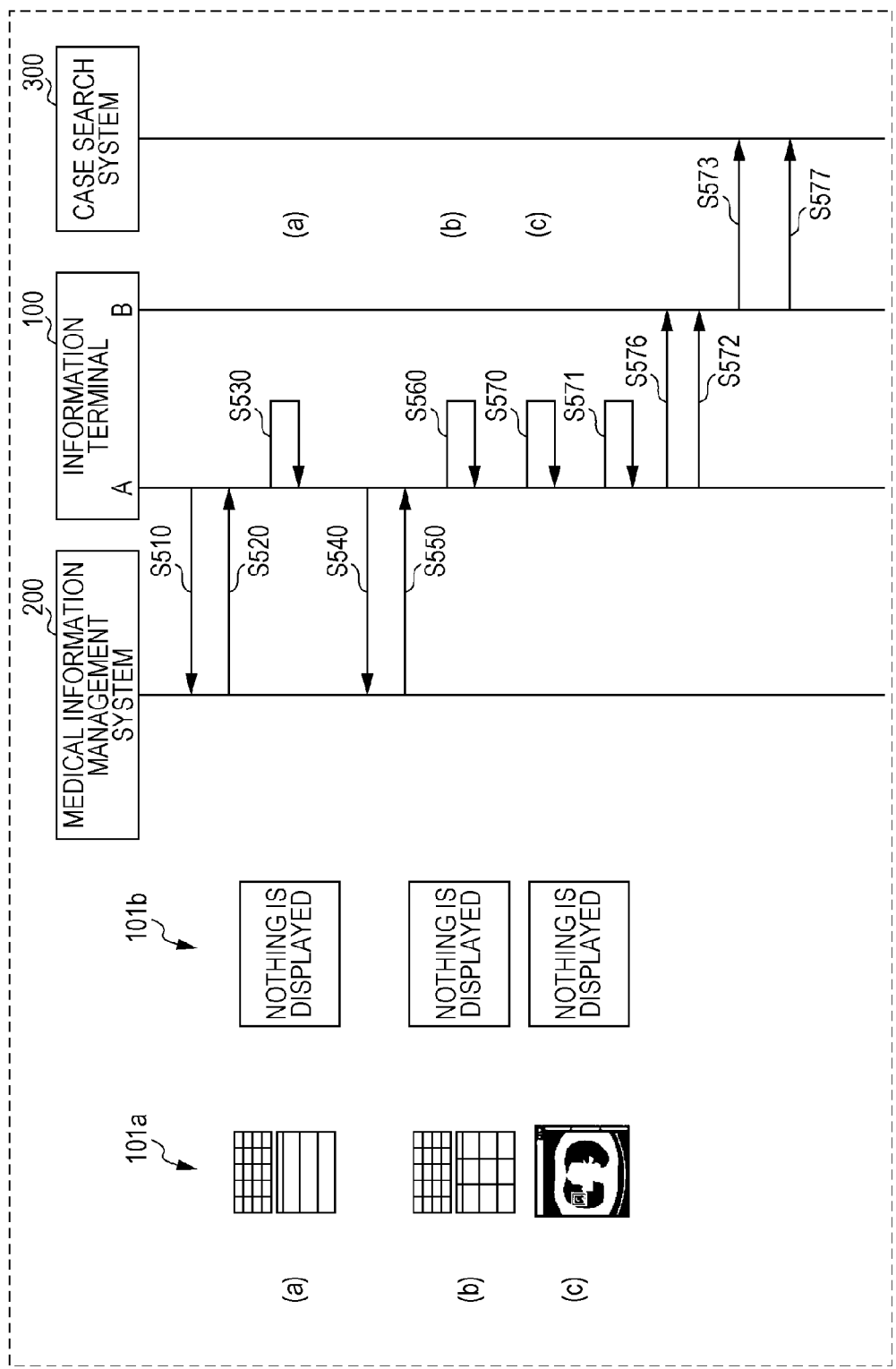
FIG. 44 is a sequence diagram illustrating a sequence, performed in a case where no region of interest is set by a user or one or more regions of interest are set, from a step in which an information terminal acquires a target case to be diagnosed from a medical information management system and sends a similar case search request to a case search system to a step in which the case search system receives the similar case search request.

FIG. 44 is a sequence diagram illustrating a sequence, performed in a case where no region of interest is set by a user or in a case where two or more regions of interest are set, from a step in which the information terminal 100 acquires a target case to be diagnosed from the medical information management system 200 and transmits a similar case search request to the case search system 300 to a step in which the case search system 300 receives this similar case search request.

Figure 28:
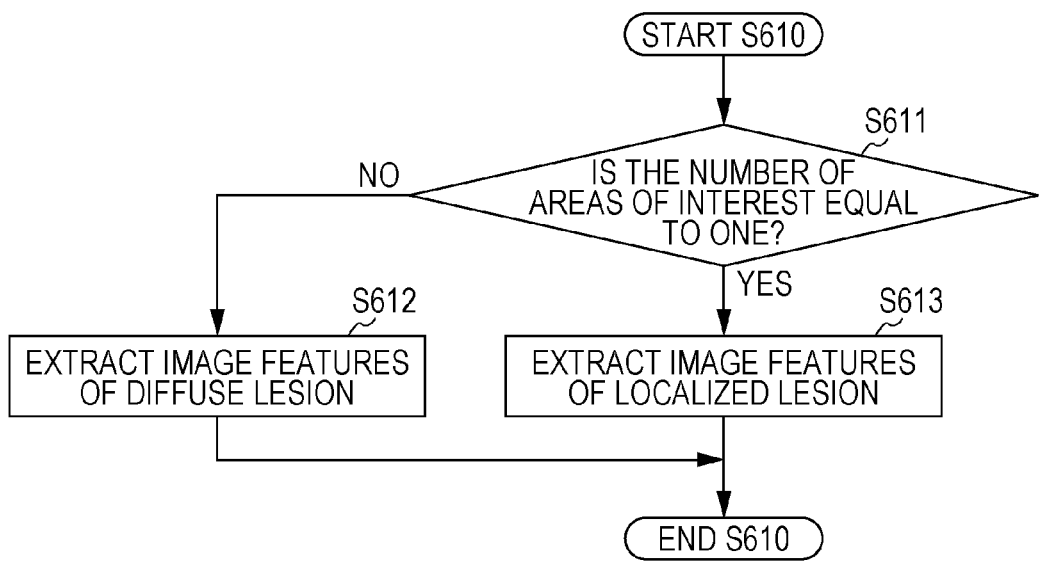
FIG. 28 is a flow chart illustrating an example of a process in S610 in FIG. 27.

S510 to S570 in FIG. 44 are similar to S510 to S570 shown in FIG. 28. After a first slice image in a selected series is displayed on the display 101a in S570, a user starts the similar case search application or sets via the operation unit 102 two or more regions of interest (ROIs) on lesions on the slice image displayed on the display 101a (S571).

Figure 21:
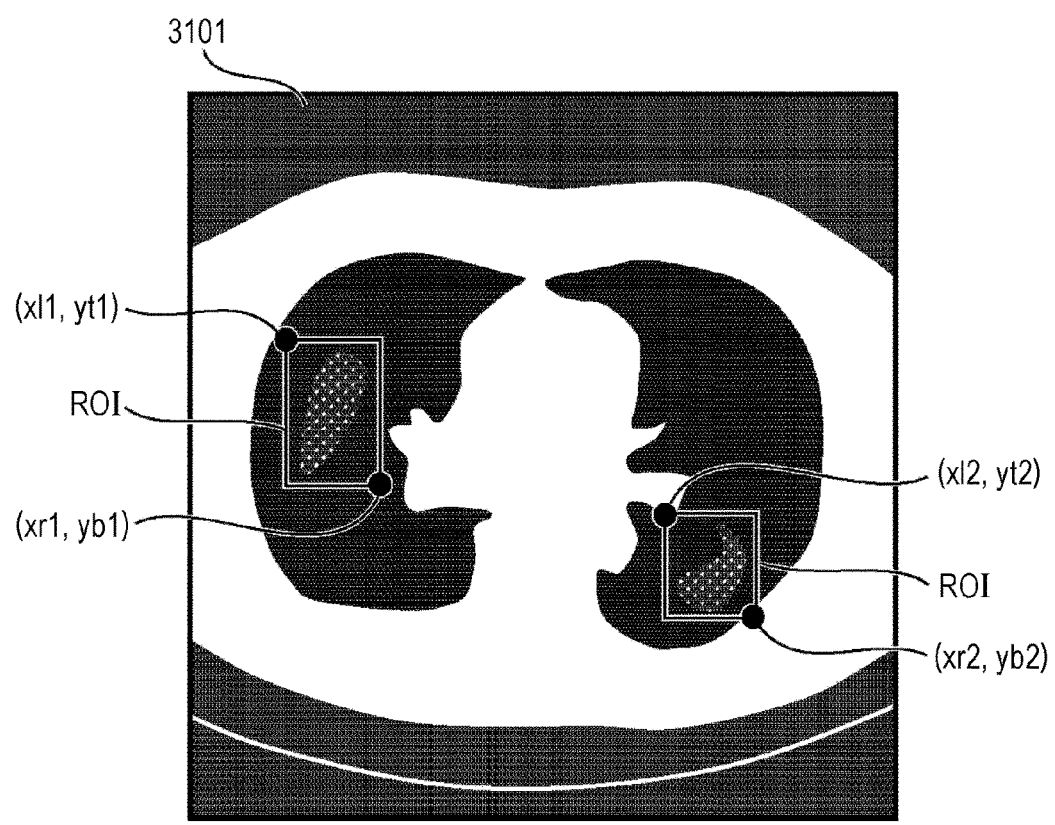
FIG. 21 is a diagram schematically illustrating two regions of interest set in a slice image of a search query image.

FIG. 21 is a diagram schematically illustrating two regions of interest set in a slice image 3101 of a search query image. In a case where there are two or more lesions on the slice image 3101 of the search query image, a user sets a plurality of regions of interest. In the example shown in FIG. 21, the two regions of interest are respectively set in the form of rectangles. Thus, a region of interest located on the left-hand side is represented by four values, i.e., coordinates (xl1, yt1) of the upper-left vertex and coordinates (xr1, yb1) of the lower-right vertex, while a region of interest located on the right-hand side is represented by four values, i.e., coordinates (xl2, yt2) of the upper-left vertex and coordinates (xr2, yb2) of the lower-right vertex.

Referring again to FIG. 44, when the operation of setting the regions of interest is detected by the input control unit 103, the ROI management unit 105 receives coordinate data of the vertices of the regions of interest from the input control unit 103 (in the example shown in FIG. 21, coordinate data of the two regions of interest (ROIs), that is, four pieces of coordinate data), and generates region-of-interest information including the received coordinate data. The ROI management unit 105 then transmits the generated region-of-interest information to the communication control unit 110 (S576). The ROI management unit 105 may generate information indicating the number of regions of interest (in the example shown in FIG. 21, the number of region of interests=2), and may put the information indicating the number of regions of interest in the region-of-interest information. In a case where the input control unit 103 detects that no region of interest is set by a user, the ROI management unit 105 generates region of interest indicating that no region of interest is set. The ROI management unit 105 may generate information indicating the number of regions of interest (in the present example, the number of region of interests=0), and may put the information indicating the number of regions of interest in the region-of-interest information. The region-of-interest information indicating that no region of interest is set may be information indicating that the number of region of interest=0. Detecting that no region of interest is set by a user may be accomplished such that when the input control unit 103 detects no operation of setting a region of interest in a particular period of time, for example, 1 minute, after starting displaying a slice image of a search query image on the display 101a in the process in S570, it is determined that no region of interest is set. Alternatively, detecting that no region of interest is set by a user may be accomplished as follows. A GUI button indicating that no region of interest is set is generated by the display control unit 104 and the generated GUI button is displayed on the display 101a. If an operation, by a user, to select the GUI button indicating that no region of interest is set is detected, it is determined that no region of interest is set. Next, in the case where the operation of setting a plurality of regions of interest is detected by the input control unit 103, the ROI management unit 105 transmits a series image of the target case to be diagnosed to the communication control unit 110 (S572).

When the communication control unit 110 receives the region-of-interest information transmitted from the ROI management unit 105, the communication control unit 110 transmits the received region-of-interest information to the communication control unit 304 of the case search system 300 (S577). Next, the communication control unit 110 receives the slice image transmitted from the ROI management unit 105 and transmits the received slice image to the communication control unit 304 of the case search system 300 (S573).

In the present example, in S571, no region of interest is set by a user or two or more regions of interest is set. This suggests that the user wants to search for a diffuse lesion which is a lesion extending over a wide area as with the example shown in FIG. 7.

In the present example, as with the example described above with reference to FIG. 22, the original series image is transmitted in S572 and S573. However, alternatively, only the series ID of the series image may be transmitted without transmitting the series image as shown in FIG. 45.

FIG. 45 is a sequence diagram illustrating an example different from that shown in FIG. 44. S510 to S570 in FIG. 45 are similar to S510 to S570 shown in FIG. 22.

In S574 following S570, the ROI management unit 105 transmits the series ID of the series image of the target case to be diagnosed to the communication control unit 110. In S575, the communication control unit 110 receives the series ID transmitted from the ROI management unit 105, and transmits the received series ID to the communication control unit 304 of the case search system 300.

In the case shown in FIG. 45, when the case search system 300 receives the series ID, the case search system 300 may acquire images corresponding to the series ID from the medical information management system 200. In FIG. 45, series images, having a possibility of being selected by a user as images to be interpreted (target case to be diagnosed) in S530 and S540, that is, all not-yet-interpreted series images are first transmitted from the medical information management system 200 to the case search system 300 (S501). Thereafter, image features of diffuse lesions are extracted in advance from these series images (S502). This makes it possible to reduce the time from specifying the series ID (S575) to starting the search in the process shown in FIG. 45.

Similar Case Search Flow

Next, a description is given below as a process from a step in which the case search system 300 performs a similar case search to a step in which the information terminal 100 displays an initial similar case search result.

Figure 27:
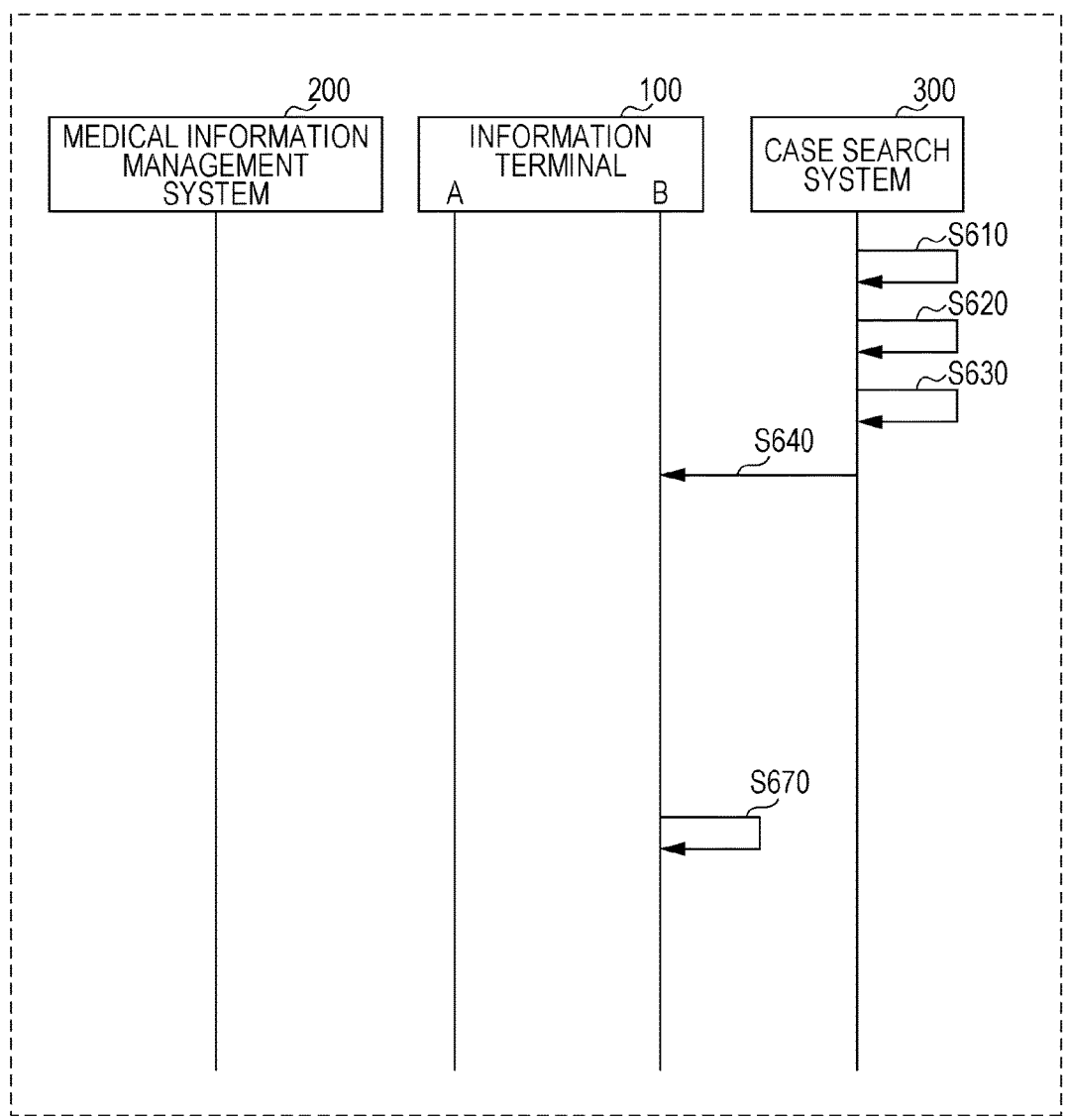
FIG. 27 is a sequence diagram illustrating a sequence from a step in which a case search system receives a similar case search request to a step in which the case search system returns a similar case search result to an information terminal.
Figure 29:
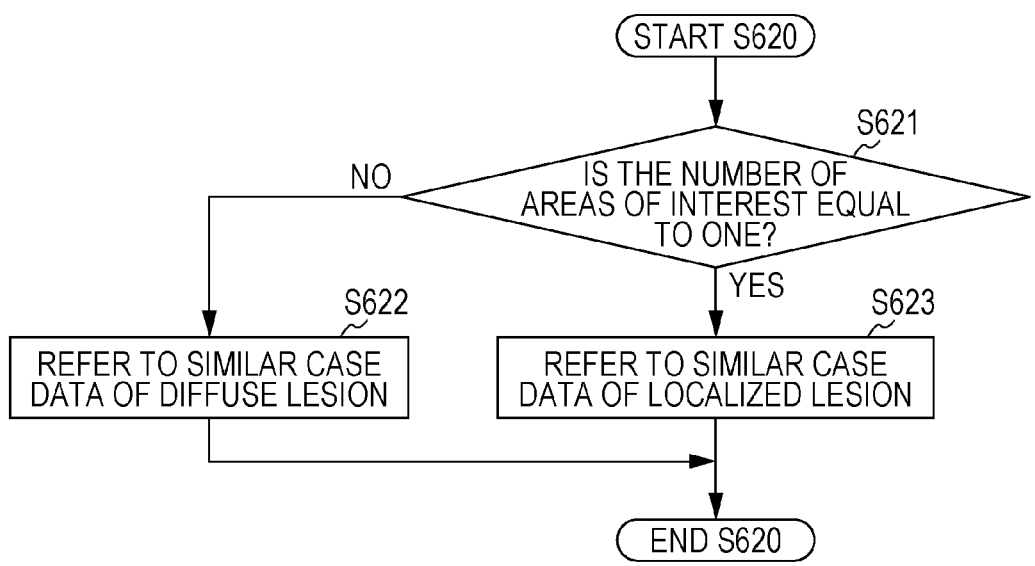
FIG. 29 is a flow chart illustrating an example of a process in S620 in FIG. 27.

FIG. 27 is a sequence diagram illustrating a sequence from a step in which the case search system 300 receives a similar case search request to a step in which the case search system 300 returns a similar case search result to the information terminal 100. FIG. 28 is a flow chart illustrating an example of a process in S610 in FIG. 27, and FIG. 29 is a flow chart illustrating an example of a process in S620 in FIG. 27.

The image feature extraction unit 302 of the case search system 300 extracts an image feature of a predetermined plurality of dimensions from the search query image (S610). In this process, as shown in FIG. 28, the image feature extraction unit 302 determines whether the number of regions of interest is equal to one or not (S611). In a case where the number of regions of interest is one (YES in S611), the image feature extraction unit 302 extracts an image feature of the region of interest in terms of the localized lesion from the region of interest set in the search query image (S613). On the other hand, in a case where the number of region of interest is equal to or equal to two or more (NO in S611), the image feature extraction unit 302 extracts an image feature of a whole internal organ in terms of the diffuse lesion from the series image of the target case to be diagnosed (to be interpreted) (S612).

As for the image feature, an image feature in terms of a shape of an internal organ or a lesion part in the medical image or an image feature in terms of a luminance distribution may be employed. For example, a 490-dimensional image feature may be employed as is disclosed, for example, in Nemoto, Shimizu, Hagiwara, Kohata, and Nawano, "Improvement of Tumor Detection Performance in Mammograms by Feature Selection from a Large Number of Features and Proposal of Fast Feature Selection Method", The transactions of the Institute of Electronics, Information and Communication Engineers. D-II J88-D-II(2), pp. 416-426, February, 2005. In the present embodiment, the image feature disclosed in this literature is employed, although other image features may be employed.

The similar case search unit 303 compares the image feature of the target case to be diagnosed (to be interpreted) extracted by the image feature extraction unit 302 with image features of respective similar case accumulated in the similar case data accumulation unit 301 (S620). In this process, as shown in FIG. 29, the similar case search unit 303 determines whether the number of regions of interest is equal to one or not (S621). In a case where the number of regions of interest is one (YES in S621), the image feature data of the region of interest extracted from the region of interest set in the search query image is compared with the image feature data 4400 registered in the similar case data 4000 (FIG. 19) of the localized lesion accumulated for each similar case in the similar case data accumulation unit 301 by calculating the distance between the two image features (S623).

On the other hand, in a case where the number of region of interest is two or more (NO in S621), the image feature data of a whole internal organ extracted from the series image of the target case to be diagnosed (to be interpreted) is compared with the image feature data 5300 registered in the similar case data 5000 (FIG. 20) of the diffuse lesion accumulated for each similar case in the similar case data accumulation unit 301 by calculating the distance between the two image features (S622).

Next, the similar case search unit 303 sorts similar cases whose distance is equal to or smaller than a threshold value in the ascending order of the distance and employs them as similar cases to be transmitted (S630). Next, the communication control unit 304 transmits the similar case data of the similar cases determined to be transmitted (S640).

Next, using the similar case data transmitted in S640, the display control unit 104 generates an initial basic screen K2 such that retrieved similar cases are displayed therein (S670).

In this process, if the number of regions of interest specified by the user is one, the basic screen K2 including axial images of similar cases such as those shown in FIG. 6 is displayed on the display 101b. On the other hand, in a case where the number of regions of interest specified by the user is two or more, the basic screen K2 including coronal images of similar cases such as those shown in FIG. 7 is displayed on the display 101b. Note that a search query image is displayed on the display 101a.

As shown in FIG. 45, in a case where image features of diffuse lesions have been extracted in advance, S612 in FIG. 28 may be removed.

Flow of Displaying Similar Case Search Result

Figure 30:
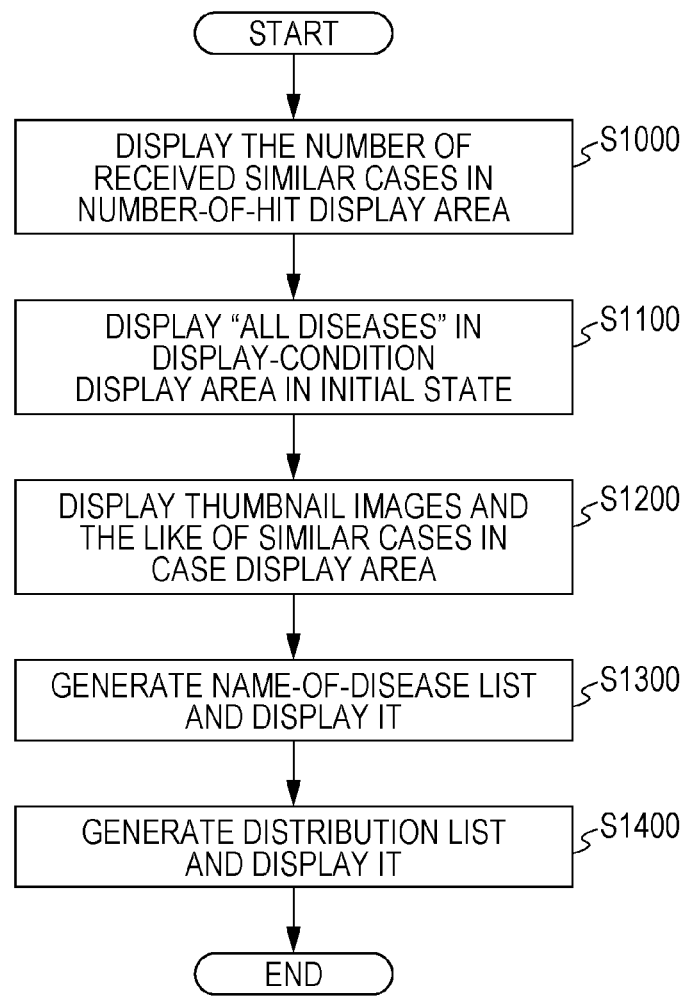
FIG. 30 is a flow chart illustrating details of a process, in S670 in FIG. 27, of generating an initial basic screen.

FIG. 30 is a flow chart illustrating details of a process, in S670 in FIG. 27, of generating the initial basic screen K2.

First, in S1000, the display control unit 104 counts the number of similar cases received in S640 in FIG. 27, and displays the value of the count in the number-of-hits display area 713.

Next, in S1100, the display control unit 104 displays "all diseases" in the display-condition display area 714. The reason why "all diseases" is displayed here is that the initial basic screen K2 represents images in the state in which narrowing according to a name of disease or a lesion distribution specified by a user has not yet performed.

Next, in S1200, the display control unit 104 selects as many thumbnail images of similar cases as can be displayed in the case display area 710 from the similar cases received in S640 in FIG. 27, and displays them in the case display area 710 together with a definitive diagnosis and a similarity level corresponding to each thumbnail image.

In the examples shown in FIG. 6 and FIG. 7, the maximum number ND of similar cases allowed to be displayed in the case display area 710 is 20. This maximum allowable number ND is determined in advance, or the maximum allowable number ND may be freely changed by a user. In a case where the number of similar cases received in S640 in FIG. 27 is larger than the maximum allowable number ND, the display control unit 104 displays a vertical scrollbar 715 on the right-side edge of the case display area 710 such that a user is allowed, by moving the scrollbar 715, to view thumbnail images of similar cases that are not displayed in the initial basic screen K2.

Next, in S1300, a name-of-disease list is generated and displayed. More specifically, first, the name-of-disease list is generated from the similar cases received in S640 in FIG. 27. The name-of-disease list is a list of the similar cases received in S640 in which the similar cases are classified according to definitively diagnosed disease names.

Here the number of similar cases received in S640 is denoted by NC. The name-of-disease management unit 108 generates the name-of-disease list based on the definitive diagnosis (broadly-classified disease name) 4700 and the definitive diagnosis (finely-classified disease name) 4800 registered in each of NC pieces of similar case data 4000. The generated name-of-disease list is managed, in the form of a table of data such as that shown in FIG. 31, by the name-of-disease management unit 108 as shown in FIG. 31.

FIG. 31 is a diagram illustrating a data structure of the name-of-disease list generated in S1300 in FIG. 30. The name-of-disease list includes fields of "disease name ID", "broadly-classified disease name", "finely-classified disease name", "number", "similar case ID". "Disease name ID is an identifier assigned to each definitively diagnosed disease name. In the present example, one disease name ID is assigned to each combination of a broadly-classified disease name and a finely-classified disease name.

"Broadly-classified disease name" is a definitively diagnosed disease name represented by the definitive diagnosis (broadly-classified disease name) 4700 registered in the similar case data 4000. "Finely-classified disease name" is a definitively diagnosed disease name represented by the definitive diagnosis (finely-classified disease name) 4800 registered in the similar case data 4000. "Number" is the number of similar cases assigned the definitively diagnosed disease name represented by the "disease name ID". "Similar case ID" is an ID identifying a similar case having a name of disease identified by "disease name ID".

The name-of-disease management unit 108 extracts the definitive diagnosis (broadly-classified disease name) 4700 and the definitive diagnosis (finely-classified disease name) 4800 for each of all similar case data 4000 received in S640, and performs classification such that a plurality of pieces of similar case data 4000 for which the definitive diagnosis (broadly-classified disease name) 4700 and the definitive diagnosis (finely-classified disease name) 4800 are the same are grouped into similar cases of the same definitively diagnosed disease name. The name-of-disease management unit 108 then counts the number of similar cases having the same definitively diagnosed disease name, and describes the value of the count in the field of "number" of a record of a corresponding definitively diagnosed disease name. Furthermore, the name-of-disease management unit 108 makes registration such that the similar case ID of each of the similar cases grouped into the same definitively diagnosed disease name is registered in the field of "similar case ID" of records of the definitively diagnosed disease name.

In the example shown in FIG. 31, a name of disease ID "DIS528" is assigned to a definitively diagnosed disease name having a broadly-classified disease name "neoplastic" and a finely-classified disease name "primary lung cancer". There are 10 similar cases assigned this definitively diagnosed disease name, and thus "10" is described in the field of "number" of a corresponding record. Similar case IDs "SIM258", "SIM551", "SIM1209", and "SIM2341", etc., assigned to the respective similar cases having the definitively diagnosed disease name described above are described in the field of "similar case ID" of the corresponding record.

The display control unit 104 then generates a name-of-disease list display area 730 based on the name-of-disease list generated in the above-described manner, and displays the resultant name-of-disease list display area 730 on the display 101.

FIG. 32, FIG. 33, and FIG. 34 respectively illustrate a first example, a second example, and a third example, of the name-of-disease list display area 730. In the first example, as shown in FIG. 32, similar cases obtained as a result of similar case search are displayed in a list in the descending order of the number of finely-classified disease names such that the corresponding numbers of finely-classified disease names are also displayed.

In the second example, as shown in FIG. 33, similar cases obtained as a result of similar case search are displayed in a list in the descending order of the number of broadly-classified disease names such that the corresponding numbers of broadly-classified disease names are also displayed.

In the third example, as shown in FIG. 34, similar cases obtained as a result of similar case search are displayed in a list in the descending order of the number of broadly-classified disease names such that the corresponding numbers of broadly-classified disease names are also displayed. Furthermore, in this third example, for each broadly-classified disease name, finely-classified disease names included in the broadly-classified disease name are displayed in a list in the descending order of the number of finely-classified disease names such that the corresponding numbers of finely-classified disease names are also displayed. In this case, definitively diagnosed disease names are represented in a hierarchical structure including a broadly-classified disease name layer and a finely-classified disease name layer.

Figure 35:
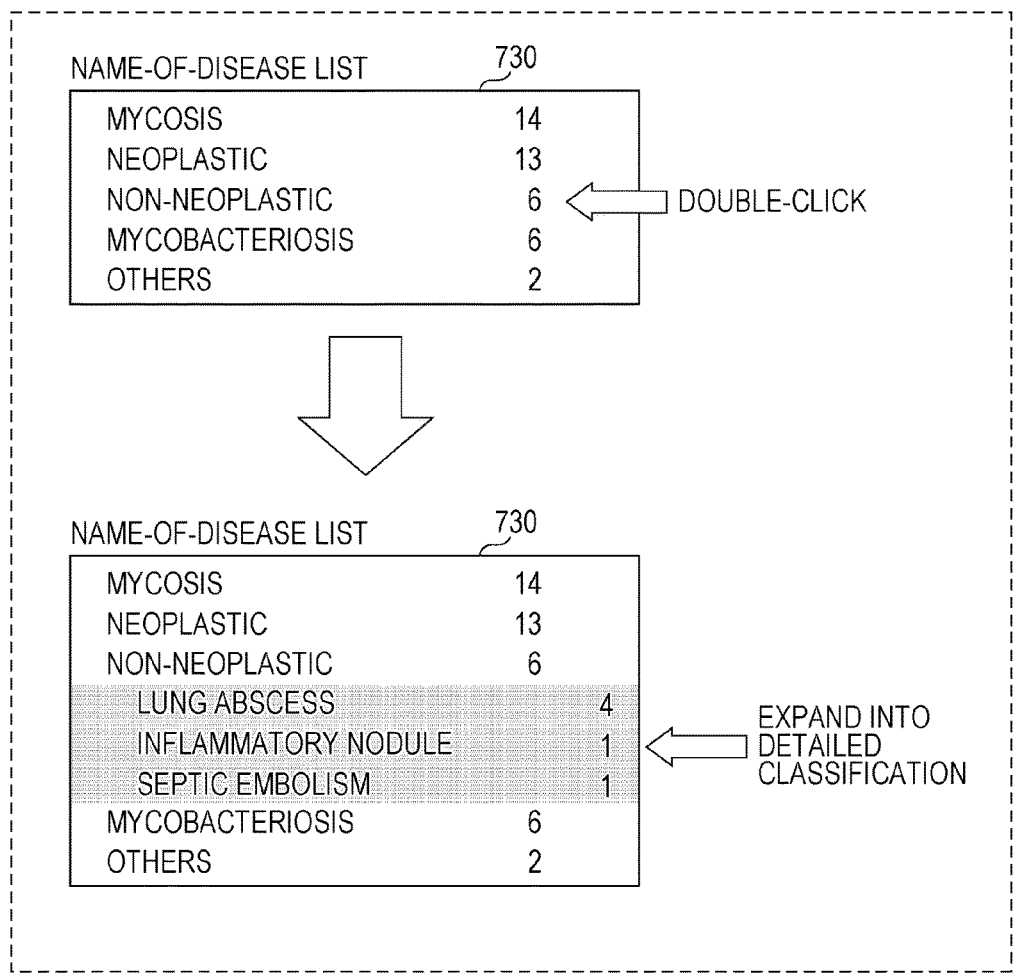
FIG. 35 is a diagram illustrating an example of a sequence of transitions of a display screen in terms of the name-of-disease list display area shown in FIG. 33.

FIG. 35 is a diagram illustrating an example of a sequence of transitions of contents displayed in the name-of-disease list display area 730 shown in FIG. 33. When an operation performed by a user to select one of broadly-classified disease names from the list of broadly-classified disease names is detected by the input control unit 103 as shown in the top area in FIG. 35, the display control unit 104 displays finely-classified disease names belonging to the selected broadly-classified disease name together with the number of finely-classified disease names in the descending order of the number as illustrated in a lower part of FIG. 35. In this name-of-disease list display area 730 displayed in the above-described manner, a user may select one of the broadly-classified disease names from the list by double-clicking or single-clicking it. In the example shown in FIG. 35, "nonneoplastic" is double-clicked, and thus finely-classified disease names belonging to the "nonneoplastic" are displayed in the form of a list.

In the lower part of FIG. 35, if a user double-clicks or single-clicks an area in which finely-classified disease names are displayed in the form of a list, then the display control unit 104 may fold the finely-classified disease names displayed in this area such that the finely-classified disease names are not displayed.

Note that the display control unit 104 may determine finely-classified disease names belonging to each broadly-classified disease name by referring to the name-of-disease list (FIG. 31). For example, in the example shown in FIG. 31, aspergillosis and cryptococcosis are related to mycosis, and thus the display control unit 104 can determine that aspergillosis and cryptococcosis belong to mycosis.

Referring again to FIG. 30, in S1400, a distribution type list is generated and displayed. More specifically, first, the distribution type list is generated from the similar cases received in S640. The distribution type list is a list of the similar cases received in S640 in which the similar cases are classified according to the lesion distributions.

The name-of-disease management unit 108 generates the distribution type list based on the lesion distribution information 4600 registered in the respective NC pieces of similar case data 4000. The generated distribution type list is managed, in the form of a table of data such as that shown in FIG. 36, by the distribution type list management unit 109.

Figures 36, 37:
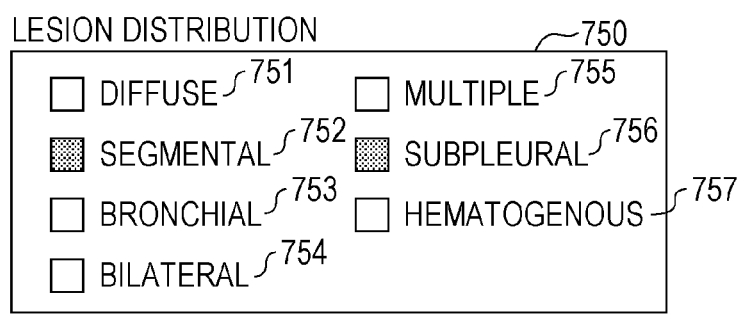
FIG. 36 is a diagram illustrating a data structure of a distribution type list generated in S1400 in FIG. 30.
FIG. 37 is a diagram illustrating a distribution type list display area generated using the distribution type list shown in FIG. 36.

FIG. 36 is a diagram illustrating a data structure of the distribution type list generated in S1400 in FIG. 30. The distribution type list includes fields of "distribution name", "number of cases", "and "similar case ID". "Distribution name" is a predetermined name of a lesion distribution type such as "diffuse", "segmental", or the like. "Number of cases" is the number of similar cases corresponding to a particular lesion distribution. "Similar case ID" is an ID identifying a similar case corresponding to a particular lesion distribution.

The distribution type list management unit 109 extracts lesion distribution information 4600 for each of all similar case data 4000 received in S640, and counts the number of lesion distributions for which the distribution type flag value is set to 1 ("false") in the extracted lesion distribution information 4600. The distribution type list management unit 109 then describes the value of the count in the field of "number of cases" of a record of a corresponding lesion distribution. Furthermore, the distribution type list management unit 109 describes a similar case ID of a similar case for which the distribution type flag value is set to 1 in the field of "similar case ID" of a record of a corresponding lesion distribution.

In the example shown in FIG. 36, there are 3 similar cases of "diffuse", and thus 3 is described in the field of "number of cases" of a record of "diffuse". Similar case IDs "SIM2521", "SIM4123", and "SIM5225" assigned to the respective similar cases of "diffuse" are registered in the field of "similar case ID" of a record of "diffuse".

The display control unit 104 then generates a distribution type list display area 750 based on the distribution type list generated in the above-described manner, and displays the resultant distribution type list display area 750 on the display 101.

FIG. 37 is a diagram illustrating the distribution type list display area 750 generated using the distribution type list shown in FIG. 36. In FIG. 36, the number of number of cases is equal to 0 for "segmental" and "subpleural", and thus "segmental" 752 and "subpleural" 756 are displayed in the inactive state in FIG. 37. The number of number of cases is equal to or greater than 1 for the other lesion distributions, and thus they are displayed in the active state.

In the present embodiment, as descried above, in the case display area 710, axial images or coronal images are switchably displayed depending on the number of regions of interest specified by a doctor or a user.

In the case where the number of regions of interest is one, it can be concluded that the doctor wants to search for localized lesions. In this case, also in the retrieved similar cases, each lesion is localized. Therefore, the display control unit 104 displays axial images including lesions in the case display area 710 in a similar manner as when a region of interest is set. This makes it possible to display images according to an intention of a doctor such that the doctor is allowed to observe details of lesions.

On the other hand, when the number of regions of interest is equal to 0 or equal to 2 or more, this suggests that the doctor wants to search for diffuse lesions. In this case, it is important to compare a lesion distribution in the search query image with lesion distributions of similar cases. However, when the number of regions of interest is equal to 0 or equal to 2 or more, if axial images are displayed, each axial image represents only one cross section of one or more lesions extending over a wide area. This makes it difficult to precisely compare the lesion distribution in the search query image with the lesion distributions of the similar cases. In the present embodiment, to handle the above-described situation, when the number of regions of interest is equal to 0 or equal to 2 or more, the display control unit 104 displays coronal images in the case display area 710 such that it is possible to see outlines of lesion distributions at a glance. This makes it possible to display images according to an intention of a doctor such that the doctor is allowed to compare lesion distributions to each other.

In the present embodiment, as described above, images of similar cases displayed in the case display area 710 are changed between axial images and coronal images depending on the number of regions of interest specified by a user. That is, in the present embodiment, by displaying coronal images in the case display area 710, it becomes possible to properly make a comparison between a search query image representing a target case to be diagnosed such as a lesion distribution of a diffuse lung disease and thumbnail images of similar cases. This makes it possible for doctors to make diagnosis with higher accuracy. Furthermore, when diffuse lung diseases are searched for, thumbnail images of similar cases are displayed in the case display area 710 as a result of the search such that it is possible to see lesion distributions in a lung at a glance. This allows it to confirm or understand similar cases in a shorter time.

Modified Embodiments (1) In the embodiments descried above, the images displayed are changed between axial images and coronal images depending on, by way of example, the number of regions of interest. However, the factor that causes the images displayed to be changed is not limited to the number of regions of interest. For example, the images displayed may be changed depending on the area size of a region of interest specified by a user.

Figure 38:
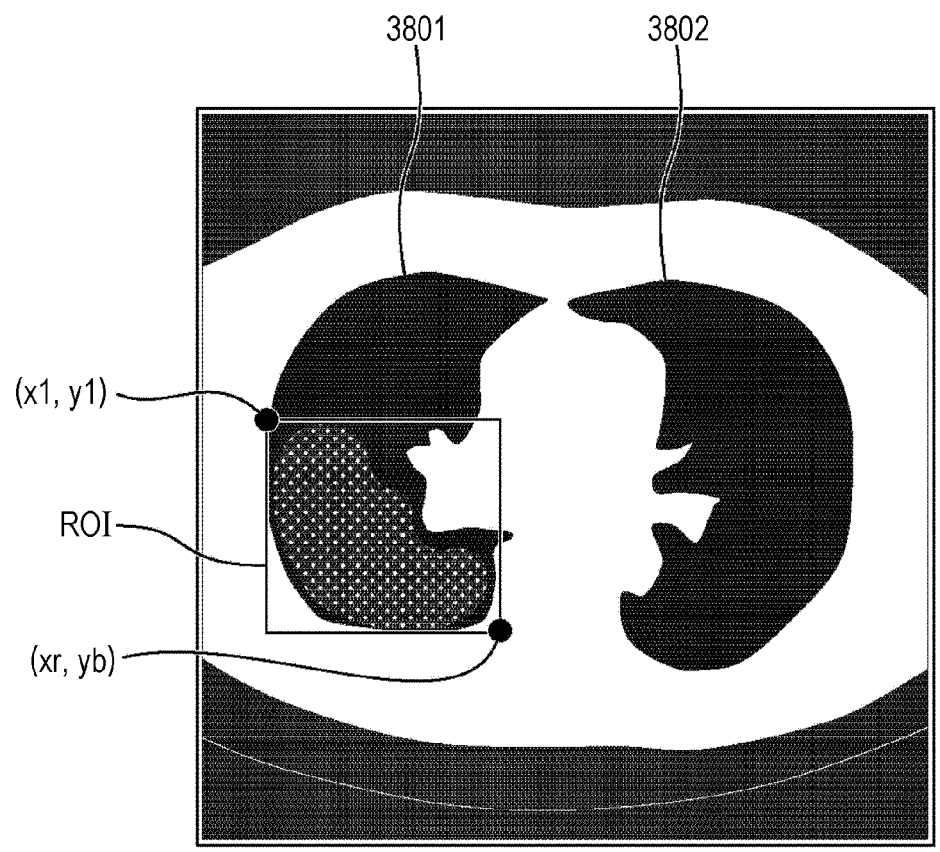
FIG. 38 is a diagram illustrating a slice image of a target case to be diagnosed in which a region of interest is set in a lesion with a large size.

FIG. 38 is a diagram illustrating a slice image of a target case to be diagnosed in which a region of interest ROI is set in a lesion with a large size. In the example shown in FIG. 38, the ratio of an overlapping area between the region of interest ROI and a lung to the total area of the whole lung including a right lung 3801 and a left lung 3802 is equal to or larger than ¼.

In the case of a search query image of a diffuse pulmonary disease, one or more lesions extends over a wide area. Therefore, a doctor is likely to set a region of interest such that a lesion extending over a wide area is enclosed in the region of interest. On the other hand, in a case where a doctor sets a region of interest for a single small area, the doctor is likely to want to search for a localized lesion. On the other hand, in a case where a doctor sets a region of interest for a single large area, for example, as shown in FIG. 38, the doctor is likely to want to search for a diffuse lesion.

Experimentally, when the ratio of the overlapping area between a region of interest ROI and a lung to the total area of the whole lung is smaller than ¼, a localized lesion is likely to be a search target, while when the ratio is equal to or larger than ¼, a diffuse lesion is likely to be a search target. In view of the above, in the present embodiment, a threshold value may be set to ¼, and the determination as to whether the search target is a localized lesion or a diffuse lesion may be made based on the value of the above-described ratio relative to the threshold value.

As for the ratio described above, a simple area size of a region of interest ROI may be employed instead of the overlapping area between the region of interest ROI and a lung. That is, the ratio used here may be a ratio of the area of the region of interest ROI to the total area of the whole lung. In the following description, the ratio of the area of the region of interest ROI to the total area of the whole lung is employed.

Figure 39:
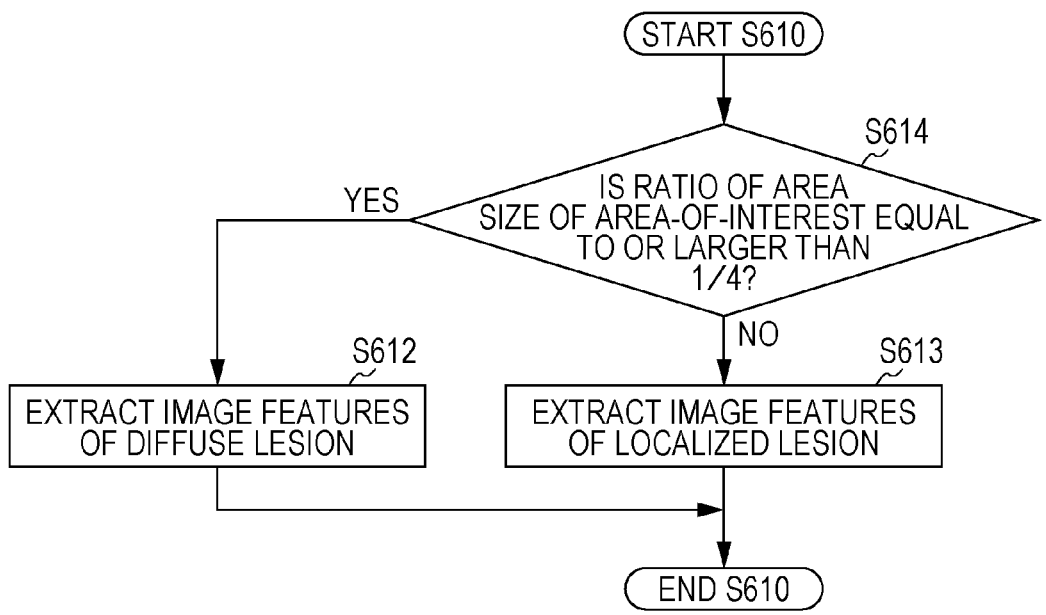
FIG. 39 is a flow chart illustrating an example, different from that shown in FIG. 28, of the process in S610 of FIG. 27.
Figure 40:
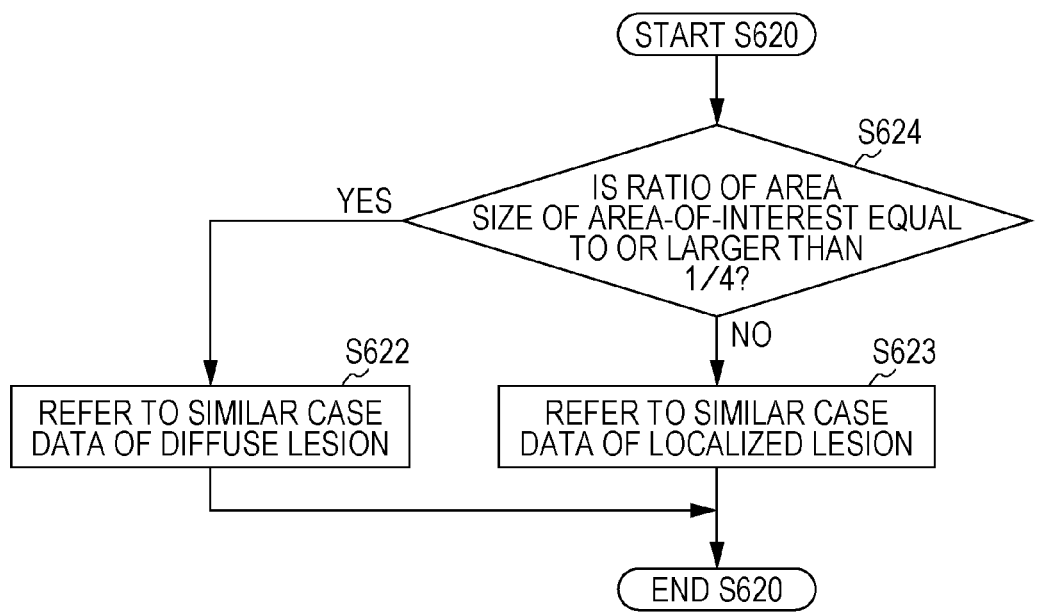
FIG. 40 is a flow chart illustrating an example, different from that shown in FIG. 29, of the process in S620 of FIG. 27.

FIG. 39 is a flow chart illustrating an example, different from that shown in FIG. 28, of the process in S610 of FIG. 27, and FIG. 40 is a flow chart illustrating an example, different from that shown in FIG. 29, of the process in S620 of FIG. 27.

In FIG. 39, first, the image feature extraction unit 302 determines whether the ratio of an area of region of interest ROI to the total area of a whole lung including a right lung 3801 and a left lung 3802 is equal to or larger than ¼. (S614). If the ratio of the area of the region of interest ROI to the area of the whole lung is equal to or larger than ¼ (YES in S614), the processing flow proceeds to S612, however if the ratio is smaller ¼ (NO in S614), the processing flow proceeds to S613. S612 and S613 are respectively similar to S612 and S613 in FIG. 28.

In FIG. 40, the similar case search unit 303 determines whether the ratio of the area of the region of interest ROI to the area of the whole lung including the right lung 3801 and the left lung 3802 is equal to or larger than ¼ (S624). If the ratio of the area of the region of interest ROI to the area of the whole lung is equal to or larger than ¼ (YES in S624), the processing flow proceeds to step S622. However, if the ratio described above is smaller than ¼ (NO in S624), the processing flow proceeds to step S623. S622 and S623 are respectively similar to S622 and S623 in FIG. 29.

In the embodiment described above with reference to FIGS. 38 to 40, in the case where the ratio of the area of the region of interest to the area of the whole lung is smaller than ¼ (FIG. 26), axial images are displayed in the case display area 710 as shown in FIG. 6. On the other hand, in the case where the ratio of the area of the region of interest to the area of the whole lung is equal to or larger than ¼ (FIG. 38), coronal images are displayed in the case display area 710 as shown in FIG. 7.

Thus, also in the embodiment described above with reference to FIGS. 38 to 40, as with the previous embodiments, it is possible to display thumbnail images in the case display area 710 so as to satisfy the intention of a doctor.

(2) In the embodiments descried above, by way of example, the case search system 300 extracts image features. Alternatively, the information terminal 100 may extract image features.

Figure 41:
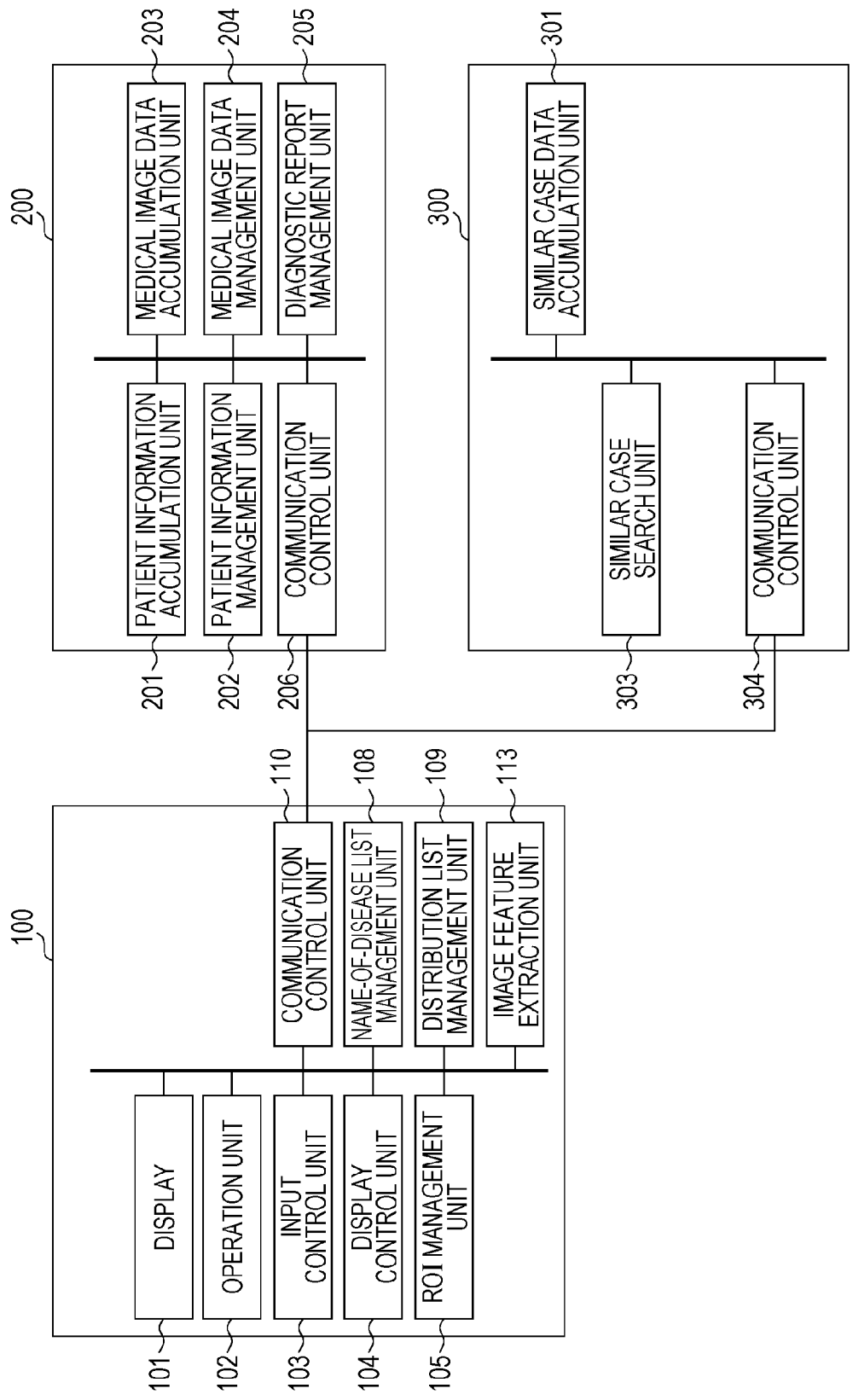
FIG. 41 is a block diagram illustrating an information terminal, a medical information management system, and a case search system, configured such that the case search system extracts an image feature.

FIG. 41 is a block diagram illustrating an information terminal 100, a medical information management system 200, and a case search system 300, configured such that the case search system 300 extracts image features.

A difference from that shown in FIG. 2 is in that the information terminal 100 additionally includes an image feature extraction unit 113, and the image feature extraction unit 302 is removed from the case search system 300.

Figure 42:
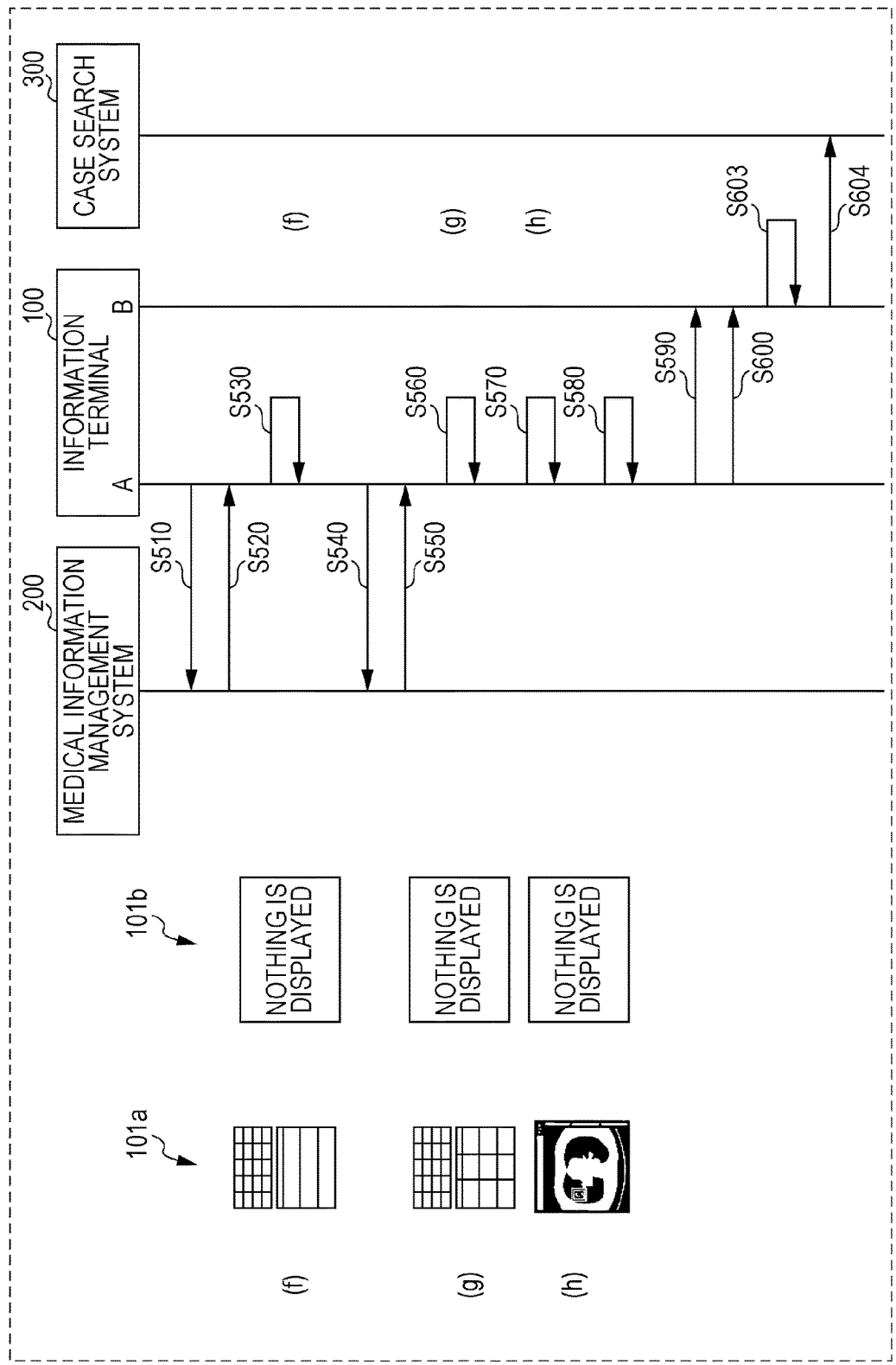
FIG. 42 is a sequence diagram illustrating a sequence from a step in which an information terminal acquires a target case to be diagnosed from a medical information management system to a step in which a case search system receives a similar case search request.

FIG. 42 is a sequence diagram illustrating a sequence from a step in which the information terminal 100 acquires a target case to be diagnosed from the medical information management system 200 to a step in which the case search system 300 receives a similar case search request.

A difference from that shown in FIG. 22 is in that after the ROI management unit 105 performs a process (S600) to transmit a slice image of a target case to be diagnosed to the communication control unit 110, the information terminal 100 extracts an image feature (S603), and transmits the extracted image feature to the case search system 300 (S604). The manner of extracting the image feature (S604) is similar to that in the case the extracting of the image feature is performed by the case search system 300.

Figure 43:
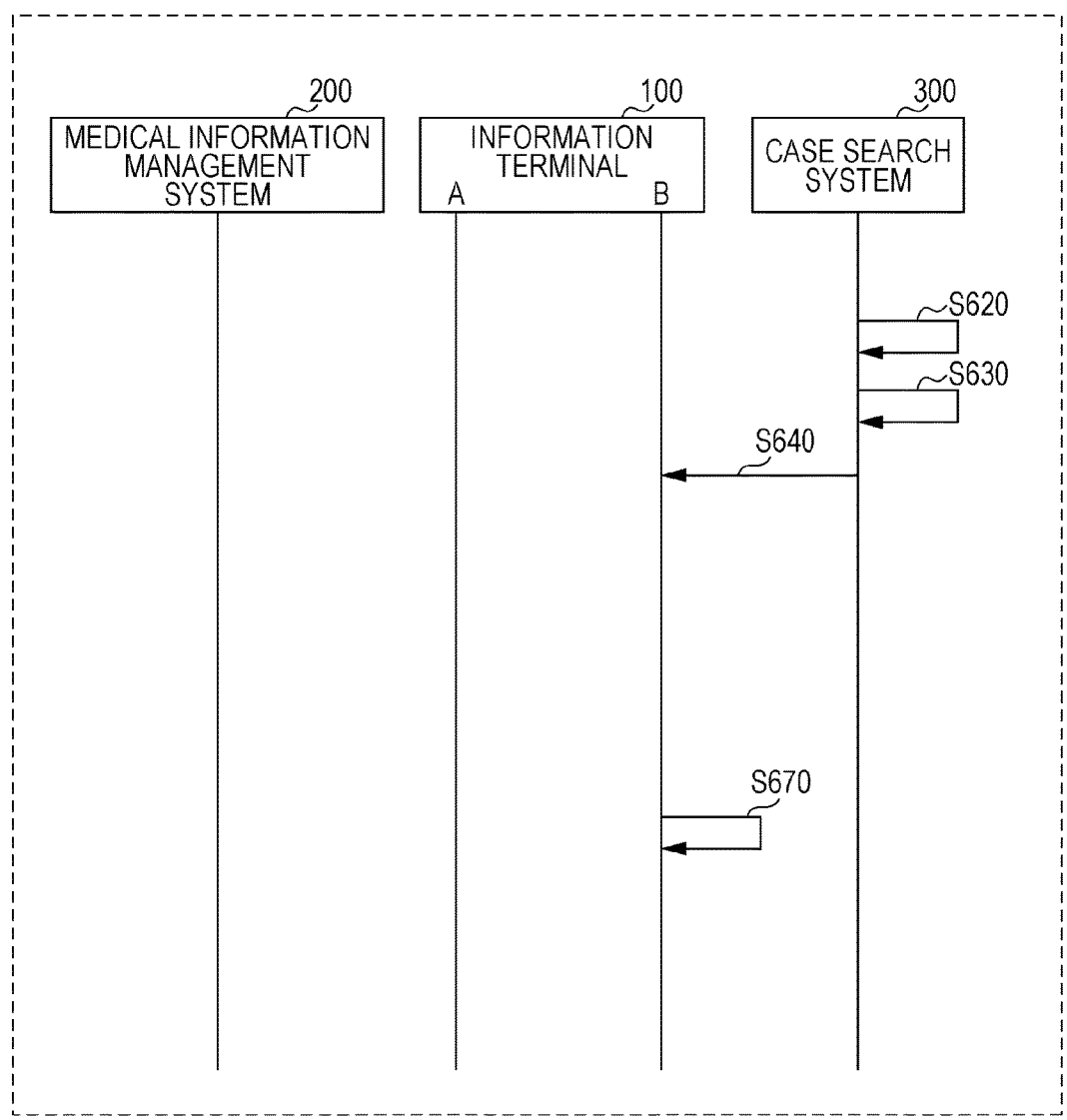
FIG. 43 is a sequence diagram illustrating a sequence from a step in which a case search system receives a similar case search request to a step in which the case search system returns a similar case search result to an information terminal.

FIG. 43 is a sequence diagram illustrating a sequence from a step in which the case search system 300 receives similar case search request to a step in which the case search system 300 returns a similar case search result to the information terminal 100. A difference from that shown in FIG. 27 is in that the image feature extraction is performed by the information terminal 100 and thus the sequence shown in FIG. 43 does not include the image feature extraction process (S610) included in FIG. 27.

The present disclosure may be applied to a similar case search apparatus that presents a similar case to be referred to in performing diagnosis using a medical image to be interpreted, and to an image interpretation training apparatus for use by medical inters, and the like.

What is claimed is:

1. A control method for an information terminal including a non-transitory computer-readable recording medium storing a program and a computer, the computer executing the program to perform the control method comprising:
   controlling the computer to detect input of information indicating a region of interest in a target medical image to be interpreted and displayed within a graphical user interface (GUI);
   controlling the computer to receive a plurality of medical images similar to the target medical image from a case search system, the received medical images having a similarity level equal to or higher than a predetermined level and including both axial images and coronal images; and
   controlling the computer to display on a display only the received axial images when a number of regions of interest indicated by the information input within the GUI indicates one, and controlling the computer to display on the display only the received coronal images when the number of regions of interest indicated by the information input within the GUI indicates two or more or when the information indicating regions of interest is not input within the GUI.

2. The control method according to claim 1, where when the number of regions of interest indicated by the input information is one, the similarity level between the region of interest of the target medical image and a region of interest of each of the medical images is equal to or higher than the predetermined similarity level, and
   when the number of regions of interest indicated by the input information is two or more or in a case where information indicating the region of interest is not input, the similarity level between a set of images including the target medical image and a set of images including the medical images is equal to or higher than the predetermined similarity level.

3. The control method according to claim 2, wherein each axial image is an image taken along a cross section of a subject such that the cross section is perpendicular to a longitudinal axis of the subject, and each coronal image is an image taken along a cross section of a subject such that the cross section is within a range of angle from 0° to 45° with respect to the longitudinal axis of the subject.

4. The control method according to claim 1, wherein
   each of the similar medical images is one of medical images included in a set of images taken by a tomographic imaging method and arranged in a first direction, and
   an axial image is a medical image that is included in the set of images and that is the greatest of all images in terms of an area size of an area corresponding to the region of interest.

5. The control method according to claim 1, wherein
   each of the similar medical images is one of medical images included in a set of images taken by a tomographic imaging method and arranged in a first direction, and
   when information indicating the region of interest is input, a coronal image is a medical image that is included in the set of images and that is the greatest of all images in terms of an area size of an area corresponding to the region of interest.

6. The control method according to claim 1, wherein the control method further comprising:
   controlling the computer to transmit information indicating a feature value of the region of interest to the case search system; and
   controlling the computer to receive the feature value of the region of interest and a plurality of similar medical images with a similarity level equal to or higher than the predetermined degree of similarity.

7. The control method according to claim 1, wherein the control method further comprises:
   controlling the computer to transmit the target medical image and information indicating the region of interest to the case search system; and
   controlling the computer to receive a feature value of the region of interest and a plurality of similar medical images with a similarity level equal to or higher than the predetermined degree of similarity, the feature value and the similar medical images being obtained based on the target medical image and the information indicating the region of interest.

8. A non-transitory computer-readable storage medium including a control program for causing an information terminal including a processor to execute a process comprising:
controlling the computer to detect input of information indicating a region of interest in a target medical image to be interpreted and displayed within a graphical user interface (GUI);
controlling the computer to receive a plurality of medical images similar to the target medical image from a case search system, the received medical images having a similarity level equal to or higher than a predetermined level and including both axial images and coronal images; and
controlling the computer to display on a display only the received axial images when a number of regions of interest indicated by the information input within the GUI indicates one, and controlling the computer to display on the display only the received coronal images when the number of regions of interest indicated by the information input within the GUI indicates two or more or when the information indicating regions of interest is not input within the GUI.

9. A control method for an apparatus including a processor to execute a process, the control method comprising:
receiving one or more regions of interest in a target medical image to be interpreted and displayed within a graphical user interface (GUI), each of the one or more regions of interest being a continuous area;
receiving a plurality of medical images similar to the target medical image from a case search system having a similarity level equal to or higher than a predetermined level, the received medical images including both axial images and coronal images; and
outputting only a first thumbnail image as a received axial image to be displayed on a display of the GUI when a total number of the one or more regions of interest is one and outputting only a second thumbnail image as a received coronal image to be displayed on the display of the GUI when the total number of the one or more regions of interest is two or more.

10. The control method according to claim 9,
wherein a similarity level between the region of interest and a region of interest of the axial image is equal to or higher than a predetermined level,
a similarity level between a first set of images including the target medical image and a second set of images including the coronal image is equal to or higher than a predetermined level, and
the first set of images are obtained through one medical examination performed on a first subject and the second set of images are obtained through one medical examination performed on a second subject.

11. The control method according to claim 9,
wherein the axial image is an image taken along a first cross section of a third subject and the first cross section is perpendicular to a longitudinal axis of the third subject, and
the coronal image is an image taken along a second cross section of the second subject and the second cross section is within a range of angle from 0° to 45° with respect to the longitudinal axis of the second subject.

* * * * *